United States Patent
Fukunaga et al.

(10) Patent No.: US 6,439,231 B1
(45) Date of Patent: *Aug. 27, 2002

(54) ARTIFICIAL VENTILATION SYSTEMS AND COMPONENTS THEREOF, AND METHODS FOR PROVIDING, ASSEMBLING AND UTILIZING SAME

(75) Inventors: Atsuo F. Fukunaga; Blanca M. Fukunaga, both of Rancho Palos Verdes, CA (US)

(73) Assignee: Medlis Corp., Rancho Palos Verdes, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/322,795

(22) Filed: May 28, 1999

Related U.S. Application Data

(60) Continuation-in-part of application No. 09/018,540, filed on Feb. 4, 1998, now Pat. No. 5,983,896, which is a division of application No. 08/751,316, filed on Nov. 18, 1996, now Pat. No. 5,778,872.

(51) Int. Cl.⁷ ............................. A61M 16/00; A62B 9/06
(52) U.S. Cl. ............................. 128/207.14; 128/202.27; 128/911; 128/912; 128/914
(58) Field of Search ....................... 128/200.14, 200.18, 128/200.24, 202.27, 203.26, 204.18, 204.22, 204.25, 204.26, 205.12, 205.17, 205.27, 205.29, 206.13, 202.14, 911, 912, 914

(56) References Cited

U.S. PATENT DOCUMENTS

| | | |
|---|---|---|
| 3,556,097 A | 1/1971 | Wallace |
| 3,713,440 A | 1/1973 | Nicholes |
| 3,856,051 A | 12/1974 | Bain |
| 4,007,737 A | 2/1977 | Paluch |
| 4,148,732 A | 4/1979 | Burrow et al. |

(List continued on next page.)

FOREIGN PATENT DOCUMENTS

| | | |
|---|---|---|
| AT | 93941 | 8/1923 |
| EP | 0 462 412 A2 | 12/1991 |
| GB | 1 270 946 | 4/1972 |
| WO | WO 85/0277 | 12/1985 |
| WO | WO 91/19527 | 12/1991 |

OTHER PUBLICATIONS

Dorsch, Jerry A., M.D., Dorsch, Susan E., M.D., *Understanding Anesthesia Equipment*, Chapter 7, The Circle Absorption System, pp. 201–202 and 220–221.

(List continued on next page.)

*Primary Examiner*—John G. Weiss
*Assistant Examiner*—Joseph F. Weiss
(74) *Attorney, Agent, or Firm*—Brinks Hofer Gilson & Lione; Daniel B. Schein

(57) ABSTRACT

A method for providing assisted ventilation which avoids hypoxia and hypocapnia in which a predetermined dead space in an assisted ventilation system is provided external to the patient. The method may also be used to create normocapnia or moderate hypercapnia without causing hypoxia during assisted ventilation. Improved assisted ventilation devices, including an improved proximal terminal, improved tubular attachments and improved coaxial filters, are disclosed which are safer and less expensive to use than corresponding prior art unilimb assisted ventilation devices. Connector fittings and adapters to provide connector fittings on assisted ventilation devices are disclosed which provide positive indication of attachment of assisted ventilation devices and resist detachment of assisted ventilation devices. The devices of the present invention also reduce medical waste in comparison to prior art assisted ventilation devices. An interface is provided which incorporates the proximal terminal and other functional devices to which tubular respiratory conduits of predetermined and/or adjustable dead space volumes can be attached.

24 Claims, 12 Drawing Sheets

U.S. PATENT DOCUMENTS

| | | | |
|---|---|---|---|
| 4,188,946 A | * 2/1980 | Watson et al. ......... 128/204.22 |
| 4,232,667 A | 11/1980 | Chalon et al. |
| 4,265,235 A | * 5/1981 | Fukunaga .............. 128/200.24 |
| 4,269,194 A | 5/1981 | Rayburn et al. |
| 4,367,769 A | 1/1983 | Bain |
| 4,386,948 A | * 6/1983 | Choksi eta l. ................. 55/499 |
| 4,391,271 A | 7/1983 | Blanco |
| 4,462,397 A | 7/1984 | Suzuki |
| 4,463,755 A | 8/1984 | Suzuki |
| 4,596,246 A | 6/1986 | Lyall |
| 4,621,634 A | 11/1986 | Nowacki et al. |
| 4,637,384 A | 1/1987 | Schroeder |
| 4,657,532 A | 4/1987 | Osterholm |
| 4,809,706 A | 3/1989 | Watson et al. |
| 4,938,210 A | 7/1990 | Shene |
| 5,088,486 A | 2/1992 | Jinotti |
| 5,121,746 A | 6/1992 | Sikora |
| 5,140,983 A | 8/1992 | Jinotti |
| 5,195,527 A | 3/1993 | Hicks |
| 5,230,727 A | 7/1993 | Pound et al. |
| 5,284,160 A | 2/1994 | Dryden |
| 5,320,093 A | 6/1994 | Raemer |
| 5,377,670 A | 1/1995 | Smith |
| 5,404,873 A | 4/1995 | Leagre et al. |
| 5,546,993 A | 8/1996 | Wikefeldt |
| 5,623,922 A | 4/1997 | Smith |
| 5,647,345 A | * 7/1997 | Saul ...................... 128/201.23 |
| 5,715,815 A | 2/1998 | Lorenzen et al. |
| 5,722,391 A | 3/1998 | Rosenkoetter et al. |
| 5,778,872 A | * 7/1998 | Fukunaga et al. ..... 128/202.27 |
| 5,823,184 A | 10/1998 | Gross |
| 5,983,891 A | * 11/1999 | Fukunaga et al. ..... 128/200.24 |
| 5,983,894 A | * 11/1999 | Fukunaga et al. ..... 128/205.29 |
| 5,983,896 A | * 11/1999 | Fukunaga et al. ..... 128/207.14 |
| 6,003,511 A | * 12/1999 | Fukunaga et al. ..... 128/202.27 |

OTHER PUBLICATIONS

Andrews, J. Jeffrey., *Inhaled Anesthetic Delivery*, Anesthesia, Fourth Edition, pp. 185; and 203–207.

Byrick, R.J., et al., "Rebreathing and Co–Axial Circuits: A Comparison of the Bain and Mera F", *Canad Anaesth Soc J*, vol. 28, pp. 321–328 (1981).

Forrest, P.R., "Defective Anaesthetic Breathing Cicuit", *Canad J Anaesth*, vol. 34, pp. 541–542 (1987).

Goresky, G.V., "Bain Circuit Delivery Tube Obstructions", *Canad J Anaesth*, vol. 37, p. 385 (1990).

Hannallah, R., et al., "A Hazard Connected With Re–Use of the Bain's Circuit: A Case Report", *Canad Anaesth Soc J*, vol. 21, pp. 511–513 (1974).

Heath, P.J., et al., "Modified Occlusion Tests for the Bain Breathing System", *Anaesthesia*, vol. 46, pp. 213–216 (1991).

Jeretin, S. et al., "A Variable Deadspace Device for Use with the Engström Respirator", *Anesthesiology*, vol. 34, pp. 576–577 (1971).

Okazaki, et al., "Effect of Carbon Dioxide (Hypocapnia and Hypercapnia) on Regional Myocardial Tissue Oxygen Tension in the Dog", *Anesthesiology*, vol. 71, No. 3A, A486 (1989).

Okazaki, et al., Effect of Carbon Dioxide (Hypocapnia and Hypercapnia) on Regional Myocardial Tissue Oxygen Tension in Dogs with Coronary Stenosis, *Anesthesiology*, vol. 73, No. 3A, A549 (1990).

Okazaki, et al., "Effect of Carbon Dioxide (Hypocapnia and Hypercapnia) on Internal Mammary–Coronary Arterial Bypass Graft Blood Flow and Regional Myocardial Oxygen Tension in the Dog", *Anesthesiology*, vol. 81, No. 3A, A717 1994.

Paterson, J.G., et al., "A Hazard Associated with Improper Connection of the Bain Breathing Circuit", *Canad Anaesth Soc J*, vol. 22, pp. 373–377 (1975).

Pilbeam, Susan P., *Mechanical Ventilation*, $2^{nd}$ Ed., Mosby Year Book, St. Louis, Missouri, pp. 285–286 (1992).

Pontoppidan, H., et al., "Acute Respiratory Failure in the Adult", *New England Journal of Medicine*, vol. 287, pp. 743–752 (1972).

Robinson, S., et al., "Safety Check for the CPRAM Circuit", *Anesthesiology*, vol. 59, pp. 488–489 (1983).

Scott, P.V., et al., "Variable Apparatus Deadspace", *Anaesthesia*, vol. 46, No. 9, pp. 1047–1049 (1991).

Shapiro, B.A., et al., "Clinical Application of Respiratory Care", *Yearbook Medical Publishers, Inc.*, pp. 351–352 ("Principles of Ventilator Maintenance") (1979).

Stoyka, W., "Usefulness of the Suwa Nomogram in Patients in Respiratory Failure", *The Canadian Anaesthetists' Society Journal*, pp. 119–128 (1970).

Suwa, K., et al., "Change in $Pa_{CO2}$ with mechanical dead space during artificial ventilation", *Journal of Applied Physiology*, vol. 24, pp. 556–561 (1968).

Advertisement of the CPRAM™ Coaxial Circuits by Dryden Corporation, Indianapolis, Indiana.

Advertisement of the ACE Breathing Circuit™ by Meridian Medical Systems, Inc., Indianapolis, Indiana.

Fletcher, R., Scott, P. V., Jones, R.P., "The variable deadspace is not necessary," Correspondence reported in *Anaesthesia*, vol. 47, No. 7, pp. 623–624 (1992).

* cited by examiner

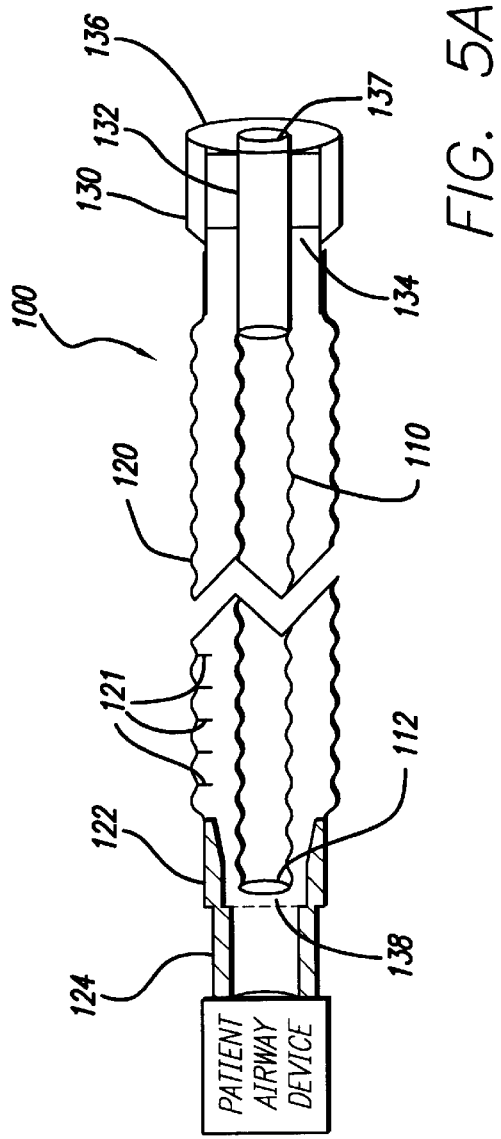
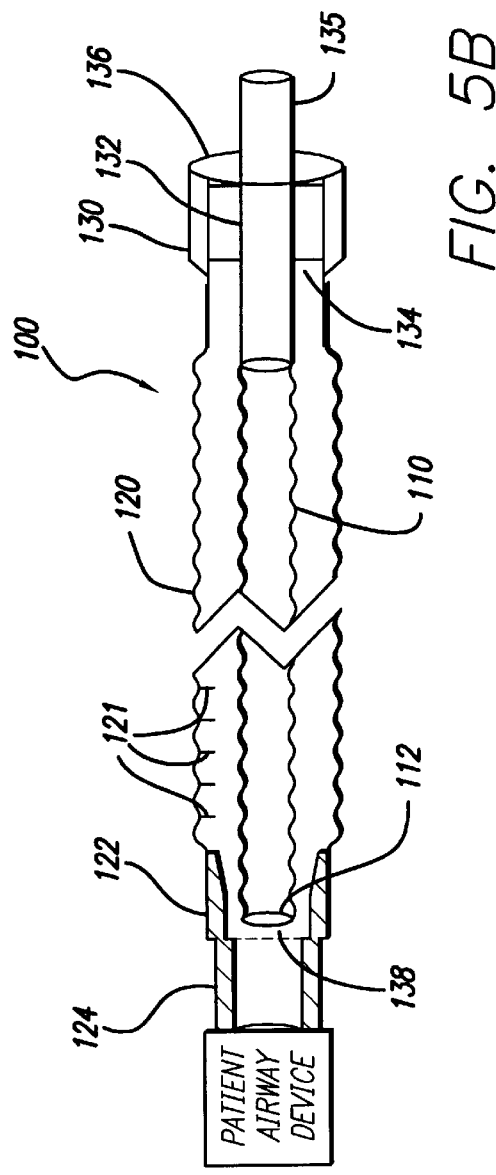

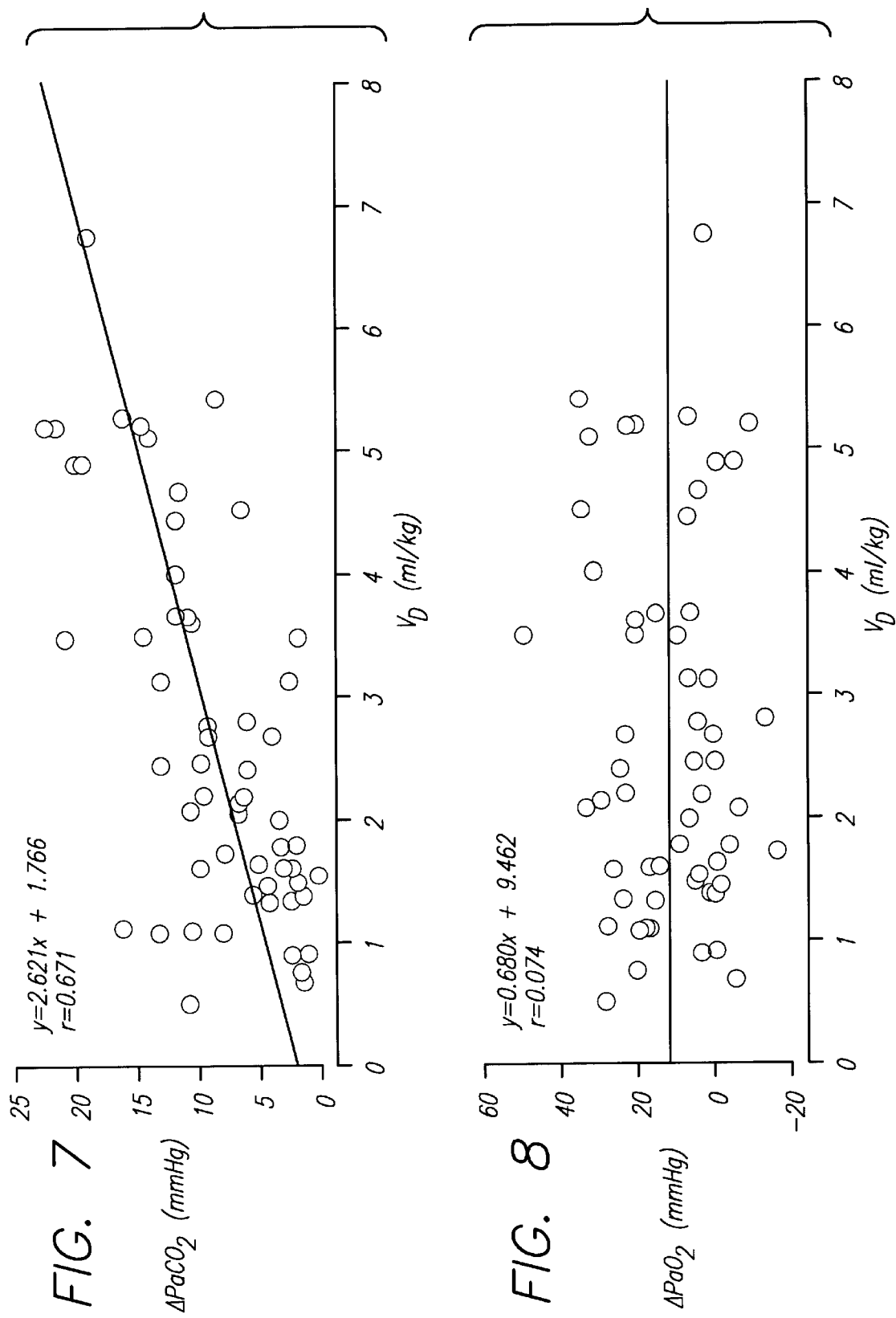

FIG. 10

THE RATE OF INCREASE IN ARTERIAL BLOOD CARBON DIOXIDE TENSION
IN RELATION TO APPARATUS DEAD SPACE

[ $\Delta PCO_2$ (mmHg) VS VD (ml) ]

| WEIGHT (kg) | DEAD SPACE VOLUME (ml) | | | | | | | | | | | | | | |
|---|---|---|---|---|---|---|---|---|---|---|---|---|---|---|---|
| | 10 | 20 | 30 | 40 | 50 | 100 | 200 | 300 | 400 | 500 | 600 | 700 | 800 | 900 | 1000 |
| 3 | 11 | 19 | 28 | 37 | 45 | 89 | 176 | 264 | | | | | | | |
| 10 | 4 | 7 | 10 | 12 | 15 | 28 | 54 | 80 | 107 | 133 | 159 | 185 | 211 | 238 | 264 |
| 20 | 3 | 4 | 6 | 7 | 8 | 15 | 28 | 41 | 54 | 67 | 80 | 94 | 107 | 120 | 133 |
| 30 | 3 | 4 | 4 | 5 | 6 | 11 | 19 | 28 | 37 | 45 | 54 | 63 | 72 | 80 | 89 |
| 40 | 2 | 3 | 3 | 4 | 5 | 8 | 15 | 21 | 28 | 35 | 41 | 48 | 54 | 61 | 67 |
| 50 | 2 | 3 | 3 | 4 | 4 | 7 | 12 | 17 | 23 | 28 | 33 | 38 | 44 | 49 | 54 |
| 60 | 2 | 3 | 3 | 3 | 4 | 6 | 11 | 15 | 19 | 24 | 28 | 32 | 37 | 41 | 45 |
| 70 | 2 | 2 | 3 | 3 | 3 | 6 | 9 | 13 | 17 | 20 | 24 | 28 | 32 | 35 | 39 |
| 80 | 2 | 2 | 2 | 3 | 3 | 5 | 8 | 12 | 15 | 18 | 21 | 25 | 28 | 31 | 35 |
| 90 | 2 | 2 | 2 | 3 | 3 | 5 | 8 | 11 | 13 | 16 | 19 | 22 | 25 | 28 | 31 |
| 100 | 2 | 2 | 2 | 3 | 3 | 4 | 7 | 10 | 12 | 15 | 17 | 20 | 23 | 25 | 28 |

$\Delta PCO_2$ (mmHg) = 2.621 × VD (ml/kg) + 1.766 (FROM STUDY II)

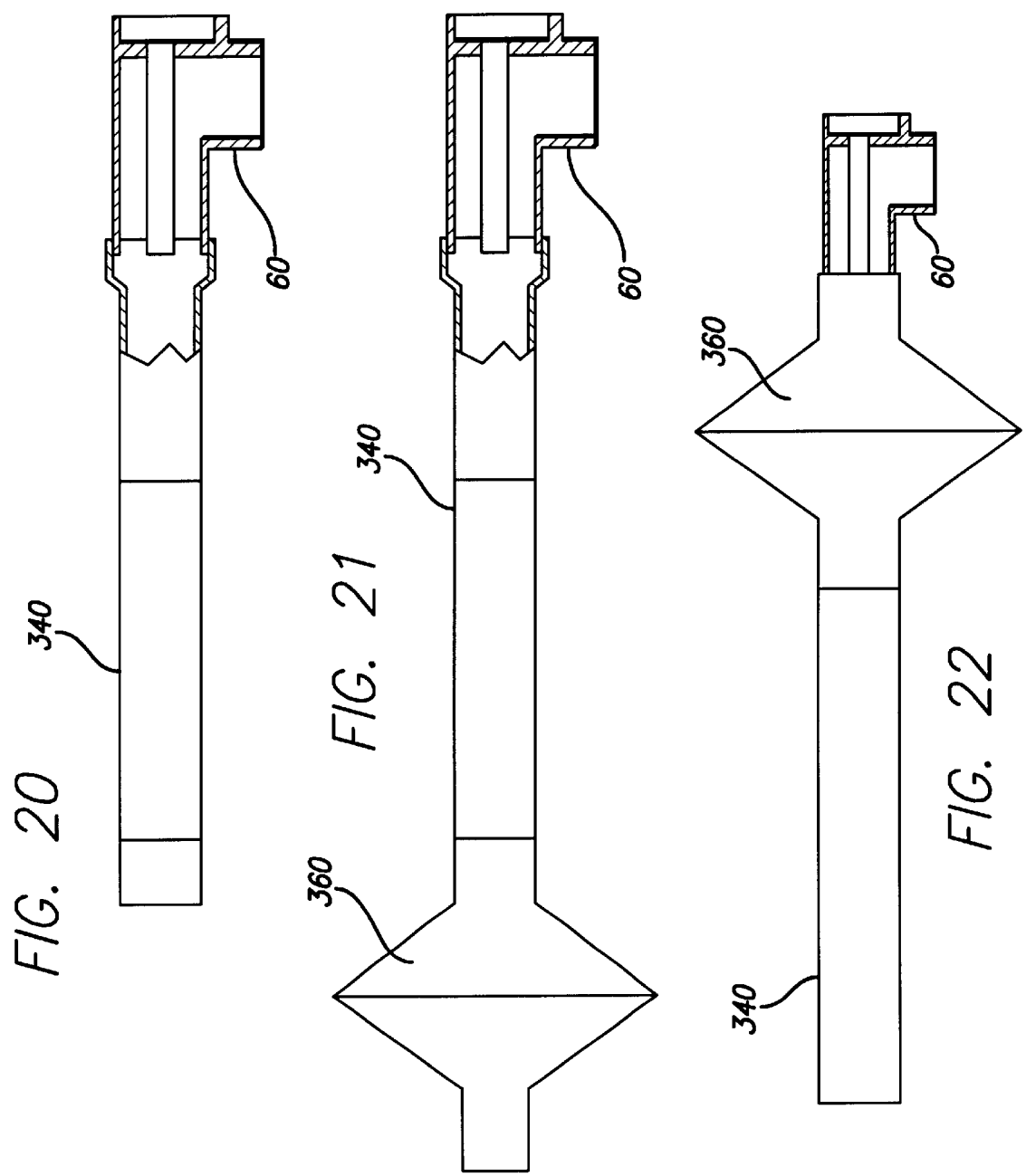

ARTIFICIAL VENTILATION SYSTEMS AND COMPONENTS THEREOF, AND METHODS FOR PROVIDING, ASSEMBLING AND UTILIZING SAME

RELATED U.S. APPLICATION DATA

This application is a continuation-in-part of U.S. patent application Ser. No. 09/018,540, filed Feb. 4, 1998, now U.S. Pat. No. 5,983,896, issued Nov. 16, 1999, which was a divisional application of U.S. patent application Ser. No. 08/751,316, filed Nov. 18, 1996, now U.S. Pat. No. 5,778,872, issued Jul. 14, 1998.

FIELD OF THE INVENTION

The present invention relates in one aspect to artificial ventilation methods and systems for administering and exhausting gases to a mammal, including methods and systems for use in anesthesia and administration of oxygen to patients, and more particularly to artificial breathing systems capable of controlling carbon dioxide rebreathing. The present invention relates in another aspect to a unilimb inspiratory and expiratory breathing device for use in a breathing circuit, which has one or more tubular conduits detachable at a common interface, the interface optionally providing for control of gas flow and operable connection to different functional devices. The present invention also relates to improved components of assisted ventilation systems and methods for providing same.

BACKGROUND OF THE INVENTION

Breathing circuits are utilized to conduct inspiratory gases from a source of same, such as from an anesthetic machine, to a patient, and to conduct expiratory gases away from the patient. The gases are conducted through two or more conduits, and, generally, at least a portion of the expiratory gas is recycled to the patient after removal of carbon dioxide. To facilitate description of the prior art and the present invention, the end of a conduit directed toward a patient shall be referred to as the distal end, and the end of a conduit facing or connected to a source of inspiratory gases shall be referred to as the proximal end. Likewise, fittings and terminals at the distal end of the breathing circuit, e.g., connecting to or directed at the patient airway device (i.e., endotracheal tube, laryngeal mask, or face mask), will be referred to as distal fittings or terminals, and fittings and terminals at the proximal end of the breathing circuit will be referred to as proximal fittings and terminals. For further information on breathing systems, and anesthetic and ventilation techniques, see U.S. Pat. No. 3,556,097; U.S. Pat. No. 3,856,051; U.S. Pat. No. 4,007,737; U.S. Pat. No. 4,188,946; U.S. Pat. No. 4,232,667; U.S. Pat. No. 5,284,160; Austrian Patent No. 93,941; Dorsch, J. A. and Dorsch, S. E., *Understanding Anesthesia Equipment: Construction, Care And Complications*, Williams & Wilkins Co., Baltimore (1974) (particularly chapters 5–7); and Andrews, J. J., "Inhaled Anesthetic Delivery Systems," in *Anesthesia. Fourth Edition*, Miller, Ronald, M. D., Editor, Churchill Livingstone Inc., New York (1986) (particularly pp. 203–207). The text of all documents referenced herein, including documents referenced within referenced documents, is hereby incorporated as if same were reproduced in full below.

U.S. Pat. No. 4,265,235, to Fukunaga, describes a unilimb device of universal application for use in different types of breathing systems, which provides many advantages over prior systems. The Fukunaga system utilizes a space saving coaxial, or tube-within-a-tube, design to provide inspiratory gases and remove expiratory gases. Generally, the inner tube is connected at its proximal end to a source of inspiratory, fresh gas, while the outer tube proximal end is connected to an exhaust port and/or to a carbon dioxide absorber (the latter at least partially exhausts into the inspiratory gas source when used in a circle system). In addition to reducing the size of the breathing apparatus connected to a patient by reducing the number of tubes near the patient, the Fukunaga system has additional benefits, such as serving as an artificial nose (expired air warms and humidifies inspired air as the opposing two flows are co-axial in the unilimb device). The Fukunaga circuit is also safer than prior co-axial systems, since the distal end of the inner tube is not connected to the outer tube at a distal fitting, so that the outer tube can be axially extended with respect to the inner tube without disconnecting the proximal end of the inner tube from the source of inspiratory gases; this safety feature can also be used to increase the dead space between the distal ends of the inner tube and outer tube, and thereby allow for adjustment of the amount of expiratory air the patient rebreaths. Dead space is defined herein as the part of the breathing circuit external to the patient which, at the end of expiration, is filled with exhaled gases to be inhaled at the next breath (generally the expired air in the dead space is combined with oxygen and/or other gases provided from a source thereof). It will be appreciated that most known breathing circuits provide a certain amount of dead space when being used. For example, in the device shown in Leagre et al., U.S. Pat. No. 5,404,873, the portion of the breathing circuit that is distal to the end to the inspiratory tube. plus the area between the face mask and the patient's face all comprises dead space where inspiratory and expiratory gases are mixed. The same is true for the device shown in Leagre, U.S. Pat. No. 5.901,705, except that the dead space also includes the interior volume of the filter.

An embodiment of the Fukunaga unilimb device is commercially manufactured as the UNIVERSAL F™ by King Systems Corporation of Noblesville, Ind., USA. The device includes a proximal terminal comprising a hollow, T-shaped housing with three ports: an inspiratory gas port, an expiratory gas port at a perpendicular angle to the inspiratory gas port, and a third ("patient") port. The proximal terminal is connected to an outer tube and a coaxial inner tube, which carry gases to and from the proximal terminal. The outer tube is flexible and corrugated, and formed of a transparent (or semi-transparent) material. The proximal end of the outer tube is sealably connected and bonded to the patient port of the proximal terminal. The proximal end of a dark colored, flexible inner tube is scalably connected and bonded to the inspiratory port, and extends through the T-shaped housing, out the patient port, and passes through most of the axial length of the outer tube. The dark color of the inner tube readily permits the user to see through the outer tube to determine whether the inner tube is properly connected.

The inner diameter of the outer tube is sufficiently larger than the outer diameter of the inner tube to permit adequate patient respiration. The distal end of the outer tube is scalably connected and bonded to the exterior of an annular housing which forms a distal terminal. The annular housing of the distal terminal is designed to prevent the distal end of the inner tube from extending beyond the distal end of the outer tube. The entire unit is designed for disposal after a single use.

The UNIVERSAL F™ device offers great advantages over prior dual line and unilimb anesthesia circuits, and respiratory assist devices. However, manufacture of the entire unit requires several complex steps, and must be done with care so that the inner and outer tubes are properly sealed and bonded to the proximal terminal ports at their proximal ends; it is particularly important that the inner tube proximal end be firmly connected to the proximal terminal (at the inspiratory port) when the inner tube carries inspiratory gases, since disconnection during use may not allow sufficient oxygen and/or anesthetic gases to reach a patient, which is highly undesirable.

While U.S. Pat. No. 4,265,235, to Fukunaga, teaches that the tubes and terminals of such a unilimb device can be detachable from one another, in practice, the proximal end of the inner tube is firmly bonded to the inspiratory port, since there remains a risk that the proximal end of the inner tube could be disconnected from the inspiratory port during use if a pressure fit (or friction fit) alone is used. Even if detachment of the inner tube is detected, the design of prior art unilimb devices does not facilitate the reconnection of the inner tube to the inspiratory port of the proximal terminal due to the need to pass the inner tube proximal end through the length of the proximal terminal via the patient port so that it can reach and be connected to the inspiratory port. Thus, the unilimb devices currently used generally comprise a proximal terminal having an integrally connected inner tube and outer tube.

Due to its single-use design, the entire unilimb device, including the distal terminal, proximal terminal, inner tube and outer tube, is disposed of after a single use, along with multiple devices usually connected to the patient nozzle, such as a $CO_2$ monitor (capnometer), temperature and humidity controlling and monitoring devices, an $O_2$ controlling and monitoring device, and an infection controlling device (e.g., a filter). Thus, in addition to the inconvenience of requiring fittings (or a housing accommodating same) for these additional devices at the patient nozzle or distal terminal, replacement of these fittings, tubing, and devices after a single use is expensive, and contributes to ever-growing medical wastes, which are sometimes difficult to find disposal sites for. All of the systems described in the aforementioned patents suffer from similar deficiencies. Therefore, there is a need for an improved unilimb device and ventilation system which reduces costs and helps the environment by reducing waste. There is also a need to simplify the construction, and to increase the safety, efficacy, and reliability of such devices.

Further, it is believed that devices sold for disposal after a single use may sometimes be reused in order to save costs, which may endanger patients. Efforts have been made to make it safer to reuse some patient respiratory conduit components. One problem with this is that the exterior of the patient respiratory conduits, as well as the interior thereof, need to be protected from contamination, so that contaminants from a first patient do not get passed on to subsequent patients by adhering to the exterior of reused components. For example, the device described in Fukunaga U.S. Pat. No. 4,265,235, discussed above, has a coaxial conduit, which can be connected at its distal end (i.e., patient end) to a filter in order to protect the interior of the coaxial conduit from being contaminated. However, the filter does not protect the exterior of the coaxial conduit from contamination. One approach to reducing contamination on the exterior of the conduit is shown in U.S. Pat. No. 5,901,705, to Leagre, in which a sleeve extends proximally from a distal (i.e., patient end) filter over the patient respiratory conduit so that at least the portion thereof nearest the patient is not exposed to contamination from the patient. The device shown in the Leagre '705 patent places a disposable filter at the patient end of the device. The Leagre device is designed to enable the breathing circuit to be reused on successive patients since the filter and sleeve prevent contamination from entering the breathing circuit from the patient; and prevent contamination in the breathing circuit from entering the patient. Thus the Leagre '705 patent teaches that the replacement of the relatively inexpensive, one-time-use filter and sleeve between patients permits the relatively more expensive breathing circuit to be used with multiple patients.

Breathing systems generally provide oxygen to a patient, while removing carbon dioxide produced by the patient. For example, in anesthesia, or intensive care, the patient is provided an artificial breathing atmosphere, in which the physician provides a mixture of gases to the patient. In addition to providing oxygen and a variety of vaporized anesthetic agents to the patient, the physician may permit the patient to rebreath some expired gases. Rebreathing simply consists of inhaling gases which have been expired, including carbon dioxide. However, assisted respiration/ventilation to a patient must be safe, and hypoxia (i.e., patient oxygen deficiency) must be avoided. Therefore, inspiratory gases are generally provided at high enough pressure, tidal volume and respiratory rate (hyperventilation) to ensure that hypoxia and atelectasis (lung alveolar collapse) is avoided. Thus, patients are given very high inspired concentrations of oxygen to avoid hypoxia, but unfortunately they often experience abnormally low carbon dioxide levels (i.e., hypocarbia or hypocapnia), and insufficient carbon dioxide can have a negative impact on vital organs (e.g., brain, heart, splanchnic organs, etc.). However, many physicians believe that increasing arterial carbon dioxide partial pressure ($P_aCO_2$, also referred to as arterial carbon dioxide tension, often reported as mmHg) in patients by increasing the carbon dioxide breathed by the patient (e.g., by increasing the amount of rebreathing) would cause hypoxia. Thus, it was believed that hypercapnia during assisted ventilation was harmful, since it was believed it would be associated with hypoxia. Further, hypocapnia, while it can be harmful, was believed to be less harmful than hypoxia. Therefore, there remains a need for an improved artificial ventilation method which controls or avoids hypocapnia without compromising vital organ tissue perfusion or oxygenation (i.e., avoids hypoxia).

Further, there is a need to increase safety of assisted ventilation systems by reducing the possibility of component disconnections during use, a need to increase the likelihood that components provided for single-use only are not reused, and that devices, such as filters, meet minimum standards to be used in assisted ventilation systems (as used herein, the terms assisted ventilation system and/or artificial ventilation system refer to any device which provides inspiratory gases to a patient and/or receives expiratory gases from a patient, such as but not limited to anesthesia machines, artificial ventilators, etc.).

SUMMARY OF THE INVENTION

The present invention provides in one aspect an improved assisted or artificial ventilation system utilizing a unilimb device for providing and exhausting gases from a mammal, and, in another aspect, an artificial ventilation method which avoids hypocapnia and hypoxia. Further aspects of the present invention include new and improved devices for use in the ventilation methods and systems of the present invention.

Aspects of the present invention relate to the surprising discovery by the inventor that concerns about disconnection of the inner respiratory tube, when connected to the inspiratory port of a proximal terminal in breathing circuits utilizing a unilimb device, such as the UNIVERSAL F™ circuit or the "Bain" circuit (U.S. Pat. No. 3,856,051), can be eliminated by the new proximal terminal construction of the present invention, which facilitates the use of tubing which is intentionally made to be readily attachable and detachable to the proximal terminal ports, rather than permanently sealably connected as in present systems, and yet provide improved function, safety, and serviceability. The breathing circuit manufacturing process is greatly simplified by eliminating the steps of sealably bonding the proximal ends of the inner and outer flexible respiratory tubes to the inspiratory and patient ports, respectively, of the unilimb proximal terminal. The new unilimb proximal terminal of the present invention facilitates the attachment and detachment of respiratory tubing to the proximal terminal, thus resulting in a cheaper and safer breathing circuit. The new unilimb proximal terminal also permits more efficient placement and utilization of the other breathing circuit components in a multifunctional interface incorporating the unilimb proximal terminal. In another aspect of the present invention, an improved coaxial tube device is provided, which is readily attachable and detachable from the new proximal terminal. The improved coaxial tube device has an inner tube in fixed spaced coaxial parallel relationship to an outer tube at its proximal end, such that a single step is required to connect both tubes to the proximal terminal. This is made possible by a fitting within or at the proximal ends of the coaxial inner and outer tubes, which still permits the distal end of the inner tube to axially move with respect to the distal end of the outer tube. As used herein, coaxial refers to the fact that one tube is contained within the other, but the central axis of both tubes need not be aligned.

Aspects of the present invention involve the surprising discovery by the inventor that hypoxia can be avoided while simultaneously creating intentional dead space in the breathing circuit, thereby increasing rebreathing of expired carbon dioxide, which enables maintenance of normal levels of arterial blood carbon dioxide (i.e., normocapnia) during artificial ventilation. Even more surprising is the discovery by the inventor that moderate hypercapnia will not cause hypoxia, provided sufficient oxygen reaches the patient; in fact, moderate hypercapnia can be beneficial to a patient (e.g., improve cardiovascular oxygen availability and tissue oxygenation). In yet another aspect of the present invention, the arterial blood carbon dioxide tension ($P_aCO_2$) can be predictably controlled via a predetermined dead space created in the unilimb device breathing tubes (i.e., the volume in the outer tube defined by the space between the outer tube distal end and the inner tube distal end). The dead space volume may be made adjustable by use of axially extendable and compressible corrugated tubing (which does not rebound to its prior length and maintains its approximate internal diameter despite bending and/or axial length changes): the tubing connects at its proximal end to the patient port of the proximal terminal, and may have dead space calibration markings thereon to permit determination and adjustment of dead space volume contained therein.

In another aspect, the present invention includes an artificial ventilation method which avoids hypocapnia and hypoxia. The method comprises provision of artificial ventilation to a mammal (in which the mammal inspires and expires spontaneously or with mechanical assistance) sufficient to prevent hypoxia, while permitting a sufficient portion of the mammal's expiratory gases to be rebreathed to allow the arterial carbon dioxide tension of the mammal to be between about 35 mmHg to about 45 mmHg (i.e., normocapnia for a human). In another aspect, the mammal's expiratory gases are rebreathed sufficiently to permit the arterial carbon dioxide tension to be between about 45 mmHg to about 95 mmHg (i.e., moderate hypercapnia). This surprising invention includes new artificial ventilation tubing and/or filters, and methods for providing same, which permits the user to provide sufficient oxygenation and carbon dioxide to a patient, while using a minimum amount of disposable, single-use materials.

Another aspect of the present invention includes an improved unilimb device useful in providing the above artificial ventilation method. In a preferred embodiment, a unilimb device for use in a breathing circuit includes an outer tube, and an inner tube, each having a proximal end and a distal end. The outer diameter of the inner tube is smaller than the inner diameter of the outer tube, wherein the outer tube can be operably connected at its distal end to a fitting (e.g., endotracheal tube or mask) that can provide artificial ventilation to a mammal. The inner tube is at least partially disposed within the outer tube, and the distal end of the inner tube is disposed within and in direct fluid communication with the outer tube. The proximal end of one of the tubes is connected to an inspiratory gas input (preferably the inner tube), and the proximal end of the other tube is connected to an exhaust outlet. The distal end of the inner tube is axially disposed at a predetermined distance from the distal end of the outer tube to create a dead space in the outer tube between the tube distal ends. The dead space permits the mixing of inspiratory (fresh) gases with expiratory gases from a patient operably connected to the device, and thereby the amount of gases rebreathed by a patient can be related to the dead space volume. This dead space can be predetermined and adjusted to provide for normocapnia or moderate hypercapnia while avoiding hypoxia. In a preferred embodiment, an inner tube and outer tube are provided, which, when operably connected to a mammal to provide respiration, the dead space external of the patient is at least 10 cubic centimeters, and in another preferred embodiment at least 30 cubic centimeters. This dead space may be as small as 10 cubic centimeters for normocarbia in a small mammal (e.g., a human infant), and may exceed 150 cubic centimeters in larger mammals (e.g., adult humans). As used herein, and as is conventionally understood, dead space may also be defined as that volume in a patient respiratory conduit external of a patient and distal of the most distal source in or connected to the patient respiratory conduit of fresh inspiratory gases to the patient, and includes the space in the conduit(s) and devices external of the patient; for example, if a single patient respiratory conduit carries inspiratory and expiratory gases, dead space is the volume in the patient respiratory conduit between the patient and the inspiratory gas inlet, and any filters or other devices therebetween. If, for example, a coaxial patient respiratory conduit is used (which, for example, has an outer flexible conduit for carrying expiratory gases from a patient operably connected to the distal end thereof), and the inner flexible tube of the coaxial patient respiratory conduit is connected to an inspiratory gas inlet, then the volume in the patient respiratory conduit (and any fittings, filters and other devices) between the patient and the distal end of inner flexible tube is dead space.

Since it is desirable to have the assisted ventilation system at a distance from the patient to permit health care personnel better access to the patient, in one embodiment of the present invention, the coaxial tubing is of considerable length, and has little or substantially no dead space therein; the distal end of the inner flexible tube is biased against or bonded to a distal fitting connected to the end of the distal end of the outer flexible tube. A dead space tube can be operably connected to the distal end of the coaxial flexible tubing; in a preferred embodiment, the dead space tube is connected to a distal fitting at the end of the coaxial tubing. The dead space tube can be operably connected through a filter (having a predetermined dead space therein) at its proximal end to the distal fitting at the distal end of the coaxial tubing (thus filtering both inspiratory and expiratory gases), or the filter may be connected at the distal end of the dead space tube. Thus, a coaxial flow of inspiratory and expiratory gases may be directed through a single filter and dead space tube. in another embodiment, the inner tube of the coaxial conduit is of a fixed length and preferably of a dark color (or has a dark colored band about its distal end); the outer tube can have its length adjusted, and is made of a clear (transparent or semi-contraction of the outer tube to alter the axial distance between the distal end of the outer tube and the distal end of the inner tube. The outer tube can be formed of a section of corrugated tubing, such as for example FLEXITUBE®, which upon axial extension from its compressed axial conformation, or vice versa, will retain its axial length (e.g., will not rebound; i.e., accordion-like pleated tubing). Further, the FLEXITUBE®, when bent, will retain the angle of curvature it is bent to without substantial reduction in the tube's inner diameter. (Suitable corrugated tubing for use in the present invention is used in the Ultra-Flex circuit from King Systems Corporation, of Noblesville, Ind., U.S.A.). The inner tube can be seen through the outer tube and, in one embodiment, the dead space volume can be determined by reference to calibration markings, which are on the outer tube, aligned with the distal end of the inner tube. By placement of a biological contamination filter between the distal ends of the inner and outer tubes and the patient port of the proximal terminal of the unilimb device, the current invention makes it possible to safely extend the service life of the proximal terminal beyond a single use. An example of suitable prior art biological contamination filter means, which can be used in some embodiments of the present invention, is the VIROBAC II Mini-Filter by King Systems. Likewise, other adapters and a variety of single use devices, previously connected at the distal or patient fittings, can be reused by connection to the interface at the proximal side of the biological contamination filter. Since the proximal terminal is more complicated to manufacture, this invention permits substantial cost savings by permitting reuse of the proximal terminal and other devices connected thereto, while simultaneously reducing environmental (medical) wastes.

In another embodiment, patient safety is enhanced by provision of unique connector fittings for connecting components of assisted ventilation systems, for example for connecting tubing and filters. For example, a unique proximal connector fitting on a filter matches and connects to a mating fitting on the distal end of either a single or coaxial patient respiratory conduit. The mating fitting on the distal end of a patient respiratory conduit may be provided with a locking device to prevent accidental disconnection. Further, patient respiratory conduits and proximal terminals may also be provided with a blocking device to prevent an unmatched dead space tube, filter, or other devices from being connected thereto. Thus, for example, only filters meeting minimum requirements can be connected to single or coaxial patient respiratory conduit having a mating fitting. In addition to filters, other devices may be provided with unique connector fittings corresponding to the unique fittings on the distal end of the patient respiratory conduit. In another embodiment of the present invention, an adaptor is provided, in which the distal end has a standard patient device connector to accommodate standard filters and patient airway devices (e.g., endotracheal tube proximal end), and the proximal end has a unique connector fitting for a mating connector on the distal end of a patient respiratory conduit.

In yet another aspect, the present invention includes a system for use in mammals to provide respiratory and other gases. The system comprises a first breathing conduit having a proximal end and a distal end for providing and exhausting respiratory gases from a mammal. and an interface comprising a breathing circuit operably connected to the proximal end of the first breathing conduit. A biological contamination filter blocks biological contaminants in the first breathing conduit from communicating with the interlace components while allowing for adequate transmission of inspiratory and expiratory flows.

The biological contamination filter can be located within the proximal end of the first breathing conduit, or serve as a separate detachable component. In one embodiment of the present invention, a coaxial filter apparatus is provided. The filter apparatus comprises an inner housing having openings at its opposite ends; at least one of the openings has an internal diameter which equals the internal diameter of the inner tube of the breathing conduit, so that the filter device may be attached in a coaxial fashion with the inner tube of the breathing conduit. The inner diameter of the filter device inner housing expands to form a chamber which accommodates a filter having a predetermined diameter to permit sufficient flow therethrough (i.e., flow resistance is inversely proportional to filter surface area). The inner housing is contained within, and in spaced parallel relationship with, an outer housing which is similar or identical in shape, but of sufficiently greater internal diameter throughout to permit fluid to flow between the outer walls of the inner housing and the inner walls of the outer housing. A single disc shaped filter may be contained within the inner housing and radially extend from within the inner housing chamber lo the outer housing chamber, or a filter in the shape of an annular ring may be disposed about the outer diameter of the inner housing filter chamber and extend to the inner wall of the outer housing chamber. The inner and outer filter housings may each be constructed from two funnel shaped components, a pre-filtration housing and postfiltration housing (which are mirror images of each other). the two components can be assembled together after placing a filter therebetween at the center of the filter chambers to be formed thereby.

A preferred embodiment of the proximal terminal interface comprises a T-shaped housing, having an inspiratory gas input (inspiratory port), an expiratory gas outlet (expiratory port), and a first respiratory (patient) port. The first respiratory port can be placed in fluid communication, through the biological contamination filter, with a first breathing (respiratory) conduit leading to a patient. The inspiratory port of the proximal terminal connects to and is integral with an internal conduit, which passes through the housing of the proximal terminal, so that the distal end of the internal conduit forms a second respiratory port, which terminates within the first respiratory port. The second respiratory port has a smaller diameter than the first respiratory port, so that gases may flow through the first respiratory port and through the space between the exterior wall of the inner conduit and the interior wall of the proximal terminal housing. The new proximal terminal of the present invention permits the ready connection and disconnection of an inner tube of a coaxial respiratory conduit to the inspiratory gas source, since direct sealed fluid communication with the inspiratory port is greatly facilitated by the inner conduit of the new proximal terminal housing. Thus, the prior art difficulties with connection of the inner tube of unilimb devices to the inspiratory port are eliminated, making it possible to avoid sealably bonding the inner flexible respiratory tube to the inspiratory port of the proximal terminal during manufacture.

It is noted that in preferred embodiments of unilimb ventilation devices, the inner tube carries inspiratory gases from an inspiratory gas source, and the outer tube carries expiratory gases. Generally, it is desired that inspiratory gas flow be laminar, while the expiratory gas flow should be turbulent. Turbulent expiratory gas flow is facilitated by the annular shape of the passage between the inner wall of the outer tube and outer wall of the inner tube, as well as by the confluence of gases exiting from the inner tube distal end into the dead space with expiratory air. Further, filtration of the expiratory gases increases turbulent flow in the outer tube, causing a positive end expiratory pressure (PEEP) effect, which helps to maintain positive pressure in the patient airway (to prevent atelectasis). Thus, the coaxial filter apparatus of one embodiment of the present invention helps create turbulent flow in the expiratory gases, when the outer tube is used as the expiratory gas conduit.

In one embodiment, the first breathing or respiratory conduit includes one tube, referred to herein for simplicity as the outer tube, and has a first (proximal) end and a second (distal) end. The outer tube is connected at its first end through a filter device to the first respiratory port, and has its second, or distal, end directed toward the patient. Both the first and second respiratory ports terminate in and are in fluid communication with the proximal end of the outer tube through one or more biological filters. Thus the first breathing conduit between the patient and the proximal terminal can comprise a single tube, the entire length of which provides a dead space, or mixing chamber for inspiratory and expiratory gases. The first breathing conduit is detachable from the proximal terminal for disposal or sterilization. Use of this system reduces costs and waste, since only the breathing conduit is designed for single use. Another advantage is that the proximal terminal of prior art unilimb devices, such as the UNIVERSAL F™, is no longer disposed of after a single use. and may be a permanent part of the interface.

In one embodiment of the present invention, the respiratory conduit may comprise an outer flexible tube, the length of which can be preselected from various lengths to vary the dead space to a preselected volume. In another embodiment, the outer tube can be axially expandable and compressible (i.e., have accordion-like pleats) to make the dead space adjustable; the dead space can be determined by reference to calibration markings on the outer tube. The calibration markings on the pleated tube may be concealed in the folded pleats, and revealed in opened pleats. The calibration markings may be color-coded bands.

In another aspect of the present invention, the first breathing conduit further comprises an inner flexible tube axially disposed within the outer flexible tube. The inner tube proximal end is connected through a biological contamination filter to the second respiratory port, and the distal end of the inner tube terminates inside of the outer tube. The dead space can be adjusted by adjusting the axial distance between the outer tube distal end and inner tube distal end. In one embodiment, the proximal end of the flexible inner tube and the proximal end of the flexible outer tube are held in spaced parallel coaxial relationship by a rigid fitting, formed of coaxial rigid annuli, a smaller annulus within a larger annulus. which are held in fixed spaced relationship by rigid radial struts extending from the exterior of the inner annulus to the interior of the outer annulus; in one embodiment, the struts do not extend to the ends of the inner annulus to permit a flexible conduit to be connected thereover. In a preferred embodiment, the fitting connects to the distal end of a filter device, which has a threaded or flanged connector at its proximal end to permit secure attachment to, and simple detachment from, the first and second respiratory ports. In a preferred embodiment, the internal conduit of the interface proximal terminal carries inspiratory gases to the second respiratory port, and the outer tube of the interface carries expiratory gases entering from the first respiratory port. The inner and outer tubes may be of predetermined lengths to provide a predetermined dead space, or the outer tube may be of variable length to permit adjustment of the dead space (or an extension added to the outer tube, with the extension having a fixed or adjustable volume or dead space); calibration markings on a clear outer tube may be aligned with the end of the inner tube to determine dead space volume.

The provision of readily accessible first and second respiratory ports in the distal end of the proximal terminal permits biological isolation of the first breathing conduit, whether it comprises only an outer tube connected to the first respiratory port, or a coaxial outer tube and inner tube, which are connected to the first and second respiratory ports, respectively. Thus, only the filter and first breathing conduit need be disposed of (or sterilized) after a single use. The new interface of the present invention permits numerous monitoring and control devices to be included in the interface at the proximal end of the biological filter(s). Various devices contained in detachable modules can be repeatedly utilized with the interface, including devices which were formerly attached to the patient nozzle and disposed of after a single-use. Thus, the new assisted ventilation system of the present invention provides for greatly simplified construction of disposable unilimb single use components, which reduces costs of production and at the same time reduces the quantity of materials requiring replacement after a single use. Further, fewer devices need be crowded about the patient, providing improved surgical safety (less clutter at the patient makes for easier surgical access and safety). Insertion of monitoring and control devices at the proximal, post filtration, end of the breathing system, permits improved control and monitoring of the patients' respiration with a simpler device.

Therefore, the present invention provides a simpler artificial ventilation system, that is easier and less expensive to construct than prior art systems, is easier, safer and less expensive to use, yet provides improved features. Further, the present invention makes possible safer artificial ventilation by providing means and a method for simultaneously preventing hypoxia and hypocapnia. Further details and advantages of the present invention will be appreciated by reference to the figures and description of exemplary embodiments set forth herein.

DESCRIPTION OF THE DRAWINGS

FIG. 5A is a cross-sectional view of an embodiment of a detachable patient coaxial breathing conduit for use in an assisted ventilation system in accordance with the present invention, such as the system of FIG. 4;

FIG. 5B is a cross-sectional view of an alternative embodiment of the detachable patient coaxial breathing conduit illustrated in FIG. 5A which includes a proximal extension;

FIG. 7 is a graphic illustration of the relationship between dead space volume, $V_D$, and the resulting change in patient arterial carbon dioxide tension, $P_aCO_2$, including a linear regression analysis curve, yielding a correlation coefficient, r, of 0.671, and a predicted value for the change in $P_aCO_2$ equal to the product of 2.621 times the $V_D$, added to 1.766; this graph illustrates that the change in $P_aCO_2$ can be reliably predicted as a function of $V_D$ (when $V_D$ is between 0 and 8 ml per kg of patient weight, or $cc^3$/kg);

FIG. 8 is a graphic illustration of the independence of $P_aCO_2$ as $V_D$ was varied between about 0 and 8 ml/kg, including a linear regression analysis curve which shows no significant correlation between the two variables in the range tested;

FIG. 10 is a table for estimating the increase in arterial blood carbon dioxide tension in relation to rebreathing circuit apparatus dead space;

FIG. 20 is partial cross-sectional view of the new proximal terminal illustrated in FIG. 3A connected to a detachable dead space tube;

FIG. 21 is partial cross-sectional view of the new proximal terminal illustrated in FIG. 3A connected to a detachable dead space tube which in turn is connected to a filter; and FIG. 22 is partial cross-sectional view of the new proximal terminal illustrated in FIG. 3A connected to a filter which in turn is connected to a detachable dead space tube.

DETAILED DESCRIPTION OF PREFERRED EMBODIMENTS

Figure 1:
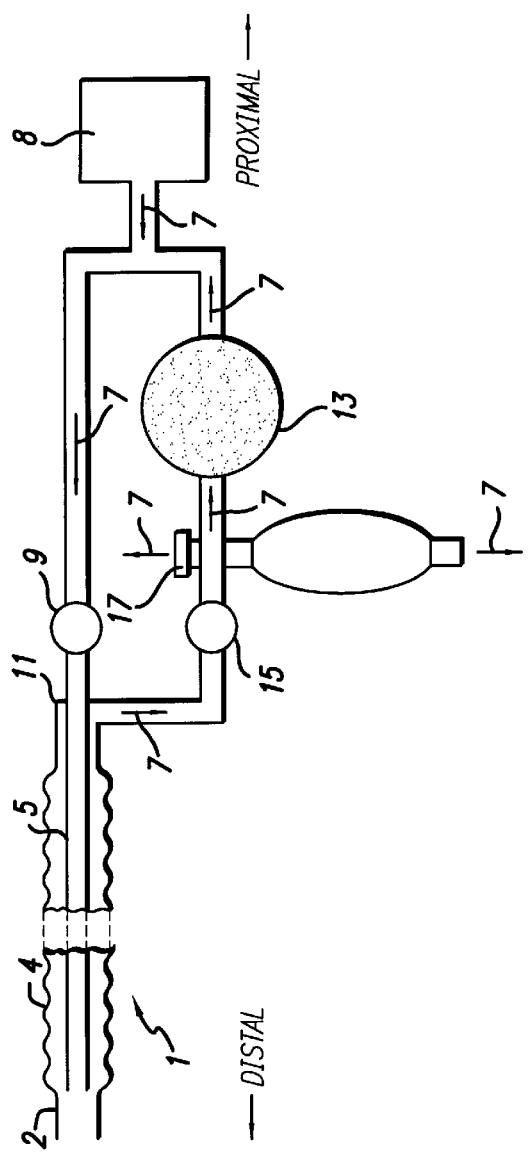
FIG. 1 is a plan and partial cross sectional view of a prior art assisted ventilation system utilizing a unilimb inspiratory and expiratory gas conduit.

A brief description of a basic prior art artificial ventilation system and unilimb device will facilitate a description of the present invention. With reference to FIG. 1, a schematic view of a circle circuit artificial ventilation system utilizing a unilimb respiratory (inspiratory and expiratory) gas conduit is illustrated. A unilimb respiratory (or breathing) conduit 1 may be attached at outlet 2 (otherwise referred to as a nozzle or distal terminal) to a patient endotracheal tube or mask. Breathing conduit I is formed to include an outer tube 4 and an inner tube 5. Directional arrows 7 show the preferred direction of gas flow through the system; for example, expiratory air is carried away from a patient through the annular spacing between inner tube 5 and outer tube 4. Inspiratory gases are provided to inner tube 5 from a gas source 8, passing through a unidirectional valve 9. Inner tube 5 penetrates the wall of proximal terminal housing 11; housing 11 essentially comprises a bend in outer tube 4, and the outer wall of tube 5 may be integrally sealed thereto.

A carbon dioxide absorber 13 may be used to remove carbon dioxide from expiratory gases passed therethrough, and the thus-filtered gases combined with inspiratory fresh gases from source 8. Expiratory gases pass from a patient outlet 2 through outer tube 4, then through unidirectional valve 15 to be recirculated or vented at exhaust port 17.

Figure 2:
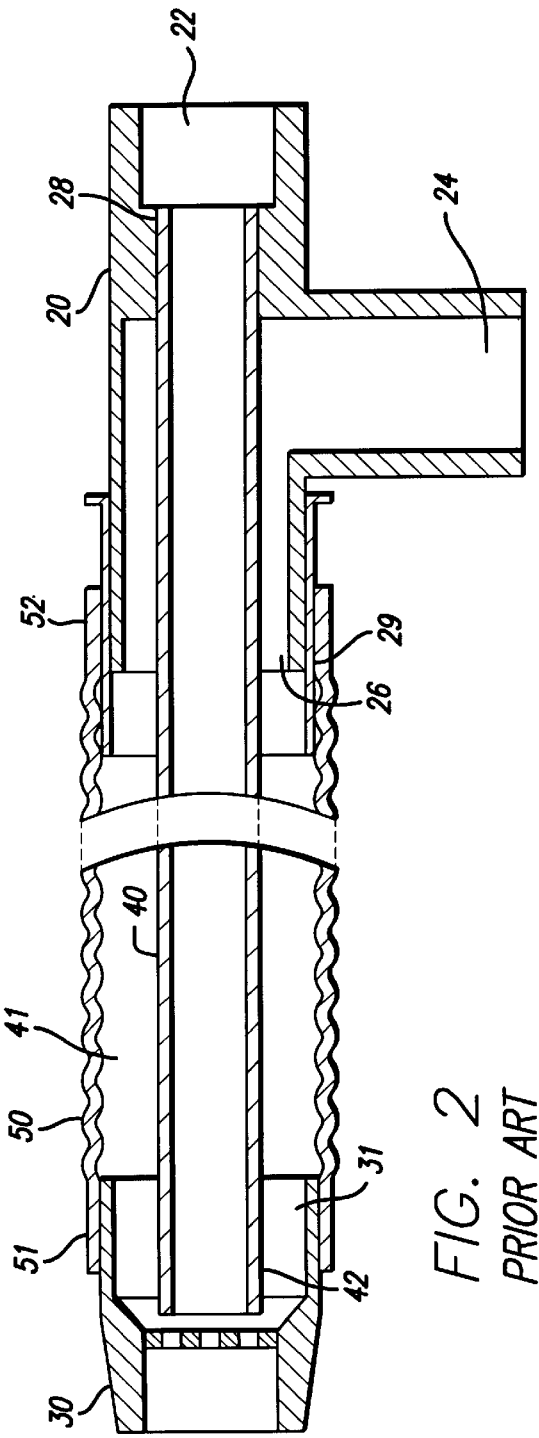
FIG. 2 is a cross-sectional view of a Fukunaga unilimb inspiratory and expiratory gas conduit and proximal terminal as described in detail in U.S. Pat. No. 4,265,235.

With reference to FIG. 2, a Fukunaga unilimb device, such as that described in detail in U.S. Pat. No. 4,265,235 is illustrated. The device comprises a T-shaped proximal terminal 20, a distal terminal 30, a flexible inner tube 40, and a flexible outer tube 50. Since the diameter of inner tube 40 is smaller than the diameter of outer tube 50, an annular space 41 is formed therebetween. The distal end 51 of outer tube 50 is connected to distal terminal 30, which has means 31 for preventing the distal end 42 of inner tube 40 from extending beyond distal terminal 30. The distal end 42 of inner tube 40 is free of terminal 30 and outer tube 50.

The T-shaped housing of proximal terminal 20 includes an inspiratory port 22, an expiratory port 24, and a patient port 26. Inner tube 40 is connected at its proximal end to inspiratory port 22, and passes partially through proximal terminal 20 and out of patient port 26. In practice, the remote location of inspiratory port 22 from patient port 26 makes it desirable to scalably bond the proximal end 28 of inner tube 40 to inspiratory port 22, or, optionally, a continuous length of inner tube 40 extends proximally of inspiratory port 22, and distally of patient port 26 to at or near distal end 51 of outer tube 50 (inner tube 40 acting to seal, or being sealably bonded to, inspiratory port 22 at the point of intersection therewith). Likewise, in order to reduce the risk that the inner tube 40 might be dislodged from inspiratory port 22, after being bonded thereto during manufacture, outer tube 50 is bonded at its proximal end 52 to the outer wall 29 of patient port 26, and is bonded at its distal end 51 to distal terminal 30.

A New Proximal Terminal

Figure 3A:
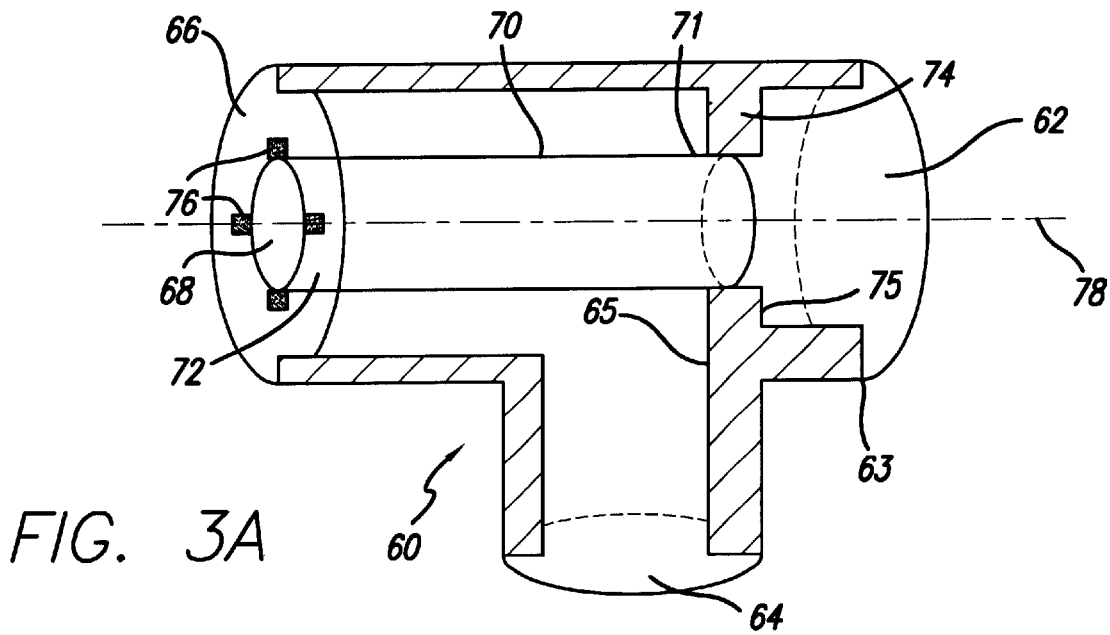
FIG. 3A is a cross-sectional perspective view of the new proximal terminal of the present invention, which includes an inner conduit connected to a second respiratory port.
Figure 3B:
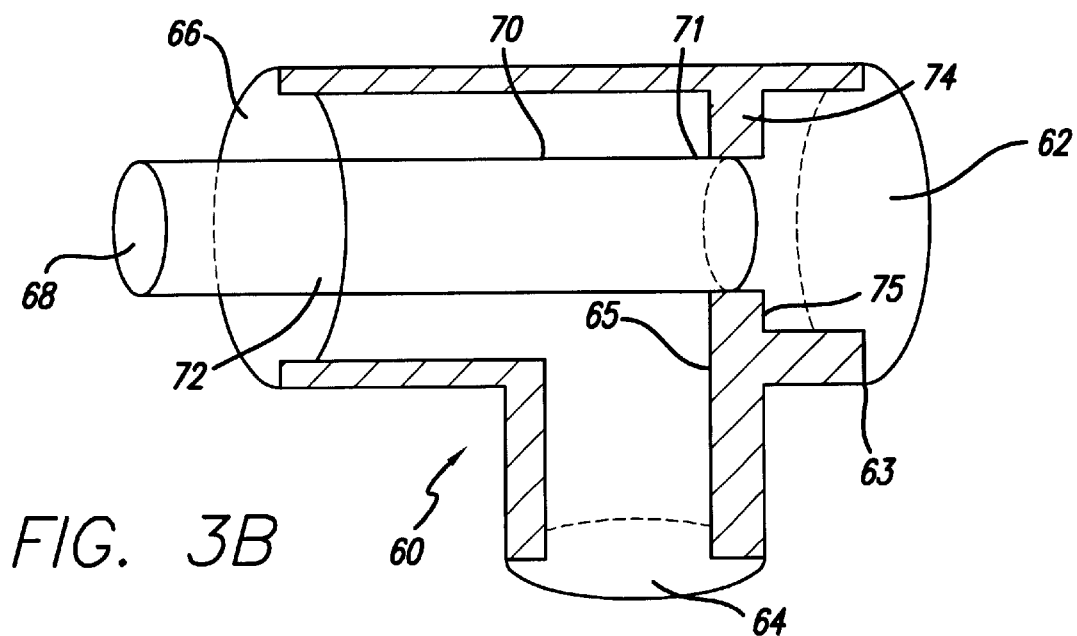
FIG. 3B is a cross-sectional perspective view of an alternative embodiment of the new proximal terminal illustrated in FIG. 3A.

With reference to FIG. 3A, a new and improved proximal terminal 60 is illustrated, which has many surprising advantages over prior art proximal terminals used in unilimb devices. Instead of having three ports, like the proximal terminal 20 of FIG. 2, proximal terminal 60 has four ports, which provide advantages and features not possible with prior art artificial ventilation systems. Proximal terminal 60 comprises a rigid, unitary T-shaped housing. having an inspiratory port 62, an expiratory port 64, a first respiratory port 66, and a second respiratory port 68. Inspiratory port 62 has a step-wise taper from a wider-diameter proximal end 63 to a narrow diameter distal end 65, although the taper may be smooth and continuous, or have other shapes. An inner conduit 70, having a proximal end 71 and a distal end 72 is sealably connected and bonded to inspiratory port 62 at fitting 74 (due to the short distance between wider-diameter proximal end 63 and the narrow diameter distal end 65, and since the inner conduit 70 is bonded into inspiratory port 62, inspiratory port 62 is considered as a single port for purposes of describing the invention, rather than described as an external port at wider-diameter proximal end 63 and as an internal port at the narrow diameter distal end 65; thus, the proximal terminal 60 is considered to have four ports if the inspiratory port is considered as a single port, but may also be considered as having five ports if the inspiratory port is considered as two ports). In a preferred embodiment, the outer diameter of inner conduit 70 is sealably bonded to distal end 65 of inspiratory port 62, so as to be integral therewith. An integral annular wall 75 forms the distal end 65 of inspiratory port 62. First respiratory port 66 and second respiratory port 68 form concentric ports about axis line 78, preferably having their concentric openings in the same plane which is perpendicular to axis line 78 of inner conduit 70. Note that second respiratory port 68, while shown axially centered or concentric, within first respiratory port 66, may be off-center with respect to axis line 78 (although this would require that at least a portion of inner conduit 70 to likewise be off-center with respect to axis line 78). In an alternative embodiment shown in FIG. 3B, inner conduit 70 may axially extend outward slightly from first respiratory port 66 so as to further facilitate connection of a tube to second respiratory port 68. Optional flanges 76 may be provided at second respiratory report 68 and/or first respiratory port 66 in order to engage matching threads or flanges of detachable tubular fittings which may be attached thereto (additional embodiments of connecting fittings are further described below with reference to FIGS. 14, 15, 16, and 19). If flexible tubing is to be connected to first and second respiratory ports by pressure fit or friction fit, the walls of the housing 60 should he sufficiently rigid to permit a firm sealed connection. The new proximal terminal may be formed of rigid plastic, such as is typically used in rigid attachments to artificial ventilation systems. Since the new proximal terminal is designed for multi-use, it may also be formed of metal, such as stainless steel. If the terminal is formed of plastic (such as that used in the UNIVERSAL F™ proximal terminal), it may be clear, translucent or opaque. It is important that the walls of the proximal terminal housing near and at the ports have sufficient rigidity to permit connection to conduits, such as the patient respiratory conduit tubes, and conduits connecting to the inspiratory and expiratory ports.

New Unilimb Artificial Ventilation System, Including New Interface

Figure 4:
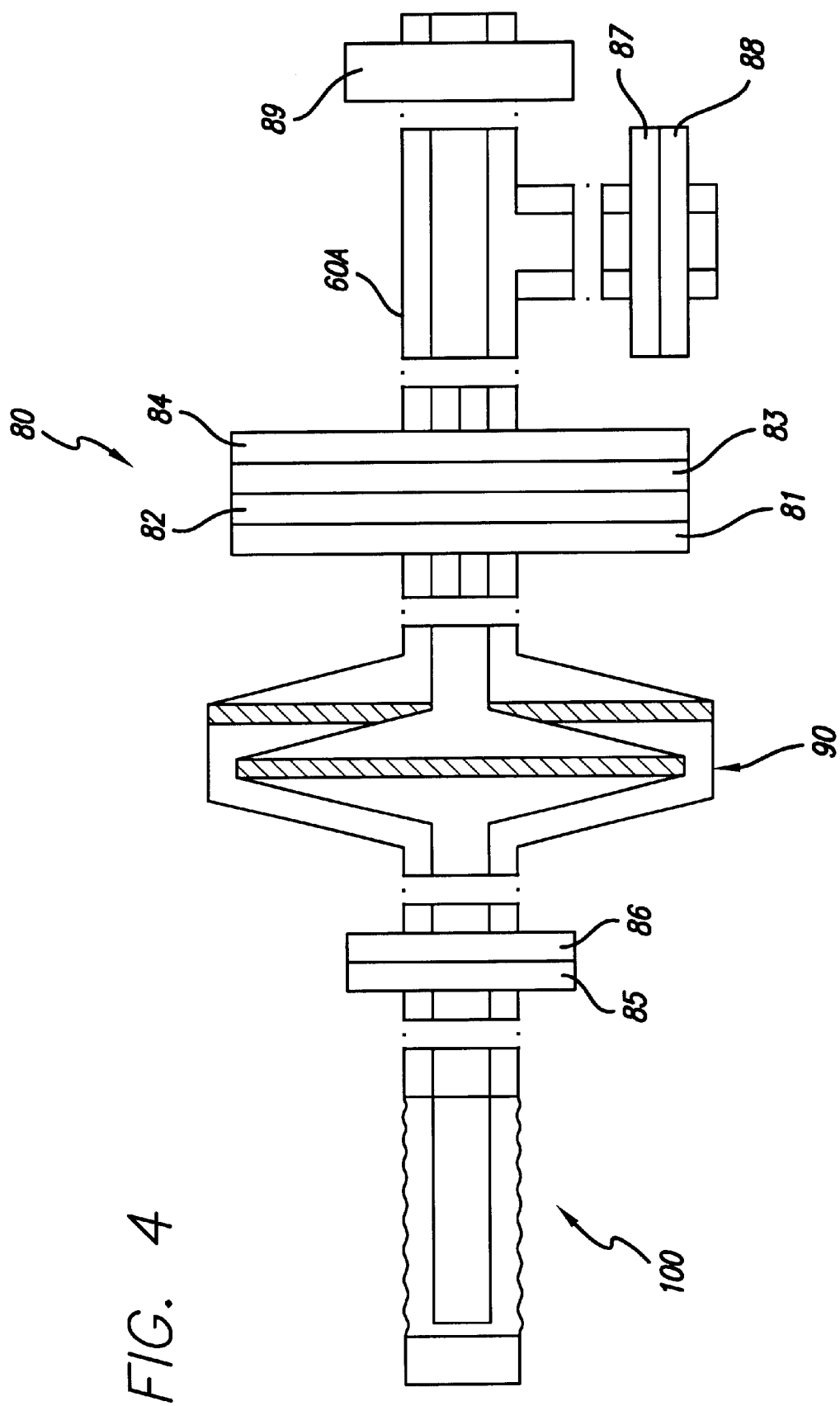
FIG. 4 is an exploded plan view of an assisted ventilation system, with optional components, in accordance with the present invention, including an interface and patient breathing conduits.

With reference to FIG. 4, an exploded plan view of an assisted ventilation system utilizing the new proximal terminal 60 of FIG. 3A is illustrated. In the embodiment of FIG. 4, a block diagram of an interface 80 is shown. Proximal terminal 60 is intended to be manufactured and shipped as a component independent of flexible breathing or respiratory conduit(s) which would lead to a patient, rather than being integrally bound (i.e., bonded) during manufacture to flexible respiratory conduits as with prior art unilimb devices. Therefore, it need not be disposed of or sterilized after a single use, and it may be incorporated in a single unit, such as interface 80, along with other functional devices 81, 82, 83, and 84, which are illustrated here in block diagram form for simplicity, or it can be placed before or after interface 80 (i.e., the new proximal terminal may be a permanent component of an assisted ventilation device or anesthesia machine). The flexibility of new proximal terminal 60 is illustrated by showing it in block form 60A. Although four functional devices 81–84 are incorporated in interface 80, more or less than this number may be used. Functional devices may be in the form of readily attachable and detachable modules, so that the ventilation system may be easily modified to meet the requirements of the user. Further, a varying number of optional functional devices, such as devices 85, 86, 87, 88, and 89 may be incorporated in the system, both proximal and distal of proximal terminal 60A.

In the embodiment of FIG. 4, a coaxial breathing conduit 100 (described in more detail below) is connected at its proximal end to functional devices 85 and 86, which in turn are connected to biological filter 90 (another embodiment of which is described in detail below). Inspiratory and expiratory gases must pass through filter 90, thus isolating interface 80, and other system components connected proximally of filter 90, from contamination (infection) by patient expiratory gases conducted by conduit 100.

In one embodiment devices 85 and 86 may comprise an $O_2$ controller (for air dilution) and a $CO_2$ controller (e.g., a rebreathing shunt hole). A reservoir bag (useful during patient transport and/or resuscitation) may be connected at, distal of, or proximal of filter 90. If the coaxial respiratory conduit is used for long term care, like in the ICU (intensive care unit and the like), devices 85 and 86 may comprise a nebulizer and a water trap. Devices 81–84, 87–89 may likewise perform control and/or monitoring functions. For example, devices in modular form can be added so that oxygen can be monitored by an oxygen sensor, and controlled by an air dilution valve; carbon dioxide can be monitored by a capnometer, and controlled by a rebreathing shunt hole; anesthetic gases can be monitored by sensors and controlled by an anesthesia machine; and temperature and humidity can be monitored by appropriate devices, and controlled by an artificial nose.

A New Patient Respiratory Conduit

With reference to FIG. 5A, an alternative embodiment of a patient breathing conduit for use with the proximal terminal of FIG. 3A is illustrated. Breathing conduit 100 consists of a flexible inner tube 110 and a flexible outer tube 120, both connected to proximal fitting 130. Inner tube 110 and outer tube 120 are kept in spaced coaxial relationship at their proximal connection to fitting 130. In one embodiment, inner tube 110 and outer tube 120 are permanently bonded to fitting 130. Fitting 130 has radial flanges 132 which keep rigid inner pipe 134 connected to but spaced from rigid outer pipe 136. Threads or flanges may be optionally provided on inner pipe 134 and/or outer pipe 136 to permit engagement with flanges or threads at second respiratory port 68 and/or first respiratory port 66, or to permit connection to a filter device, which in turn connects to second respiratory port 68 and/or first respiratory port 66.

Distal end 122 of flexible outer tube 120 connects to a rigid annular distal terminal 124. The distal end 112 of flexible inner tube 110 does not axially extend beyond distal terminal 124 or the distal end 122 of outer tube 120. The distal end 112 of flexible inner tube 110 may optionally be connected to distal terminal 124 or to the distal end 122 of outer tube 120, or may be free to move axially within outer tube 120. The distance between distal end 112 of flexible inner tube 110 and the distal end 122 of flexible outer tube 120 (as extended by distal terminal 124) defines a dead space 138. In one embodiment of breathing conduit 100, varying lengths of flexible inner tube 110 and/or flexible outer tube 120 are utilized in order to vary the size of the dead space to a predetermined volume. In another embodiment, outer tube 120 is formed of adjustable-length tubing, so that the dead space can be adjusted by extending or compressing the outer tubing axial length. Extension may be done by adding a dead space tube to the distal end of outer flexible tube 120, rather than or in addition to using an extendable, accordion-like outer flexible tube. The outer tubing may be formed of transparent or semi-transparent material, and calibration markings 121 may be included thereon to permit determination of dead space volume by alignment of the distal end 112 of inner tube 110 with the markings 121.

Distal end 122 of flexible outer tube 120 or distal terminal 124 may be provided with a positioning device, which may be formed of one or more inner tapered flanges, or a positioning ramp, with a terminating stop, so that when the distal end 122 of flexible outer tube 120 or distal terminal 124 is biased against the distal end 112 of inner flexible tube 110, the distal end 112 of flexible inner tube 110 is positioned at the desired location with respect to distal end 122 of flexible outer tube 120 or distal terminal 124, with the terminating stop preventing distal end 112 of flexible inner tube 110 from extending distally of distal end 122 of flexible outer tube 120 or distal terminal 124.

In a preferred embodiment, flexible tubes 110 and 120 are readily attachable to and detachable from fitting 130, and flexible tube 120 is readily attachable to and detachable from distal terminal 124. In one embodiment, flexible tube 110 is not utilized, so that the entire length of tube 120 constitutes dead space. In another embodiment, tube 110 and/or tube 120 connect directly to an interface, which incorporates proximal terminal 60; a biological filter is located between the proximal terminal and tubes 110 and 120.

A New Coaxial Filter

Figure 6A:
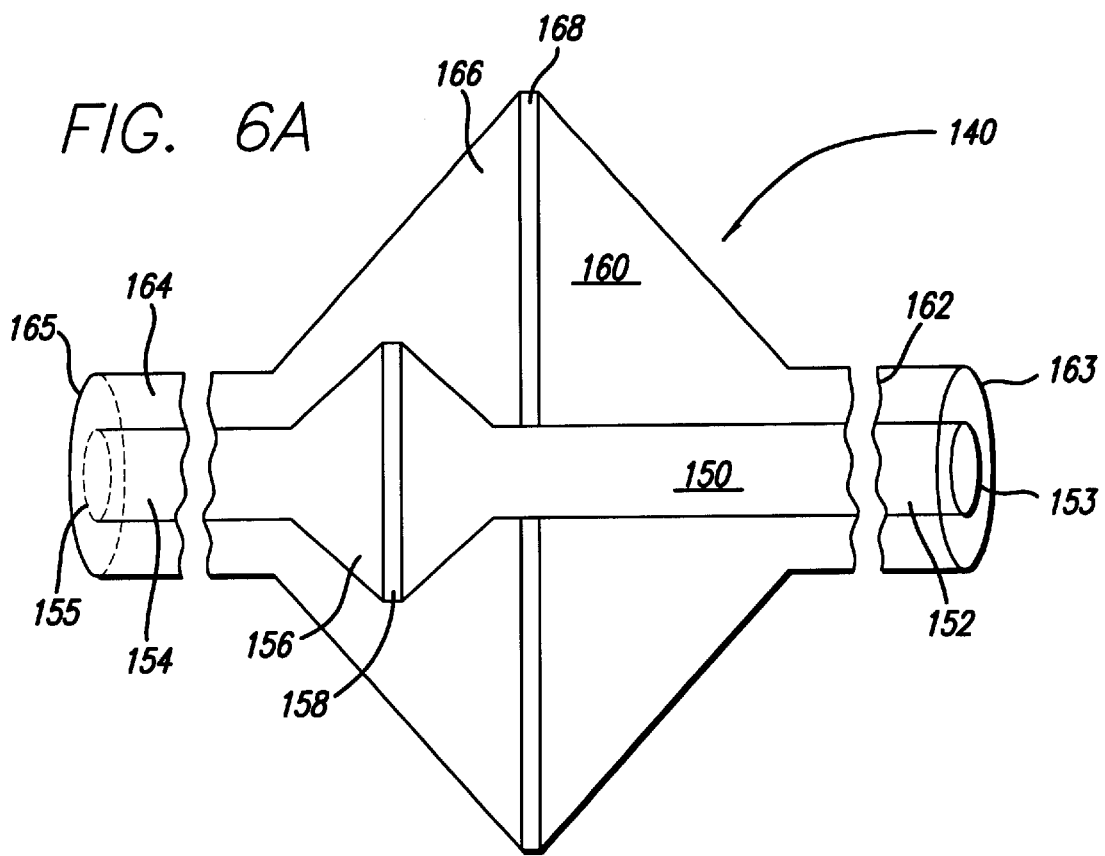
FIG. 6A illustrates a perspective, partial cross-sectional view of an embodiment of a coaxial filter device for use in an assisted ventilation system in accordance with the present invention.

With reference to FIG. 6A, a preferred embodiment of a new coaxial filter device 140 is illustrated, which can be used in a unilimb ventilation device. Filter 140 includes an inner housing 150 and an outer housing 160. Inner housing 150 is formed of tubular conduits 152 and 154 connected to opposed openings in filter chamber 156, which contains a first or inner filter 158. Outer housing 160 is formed of tubular conduits 162 and 164 connected to opposed openings in filter chamber 166, which contains a second or outer filter 168. Flanges or threads may be provided at one or more of the tubular conduit ends 153, 155, 163, and 165, so that the filter may be secured in axial relationship to other tubular fittings. In a preferred embodiment, filter device 140 is connected to a proximal terminal, such as proximal terminal 60 in FIG. 3A, so that inner tubular conduit 152 is sealably connected to the second respiratory port 68 and outer tubular conduit 162 is sealably connected to the first respiratory port 66. In a preferred embodiment, inspiratory gases pass into tubular conduit 152, pass through filter 158, and out of tubular conduit 154 into a breathing conduit, such as breathing conduit 100 illustrated in FIG. 5A, leading to a patient. Expiratory gases pass out of a breathing conduit into the annular spacing between outer tubular conduit 164 and inner tubular conduit 154; the expiratory gases then pass through filter 168, into tubular conduit 162 (i.e., the annular spacing between outer tubular conduit 162 and inner tubular conduit 152), and into the proximal terminal and out of the expiratory port of the proximal terminal, such as port 64 in proximal terminal 60 in FIG. 3A. The preceding gas flow pattern can be reversed if desired.

Figure 6B:
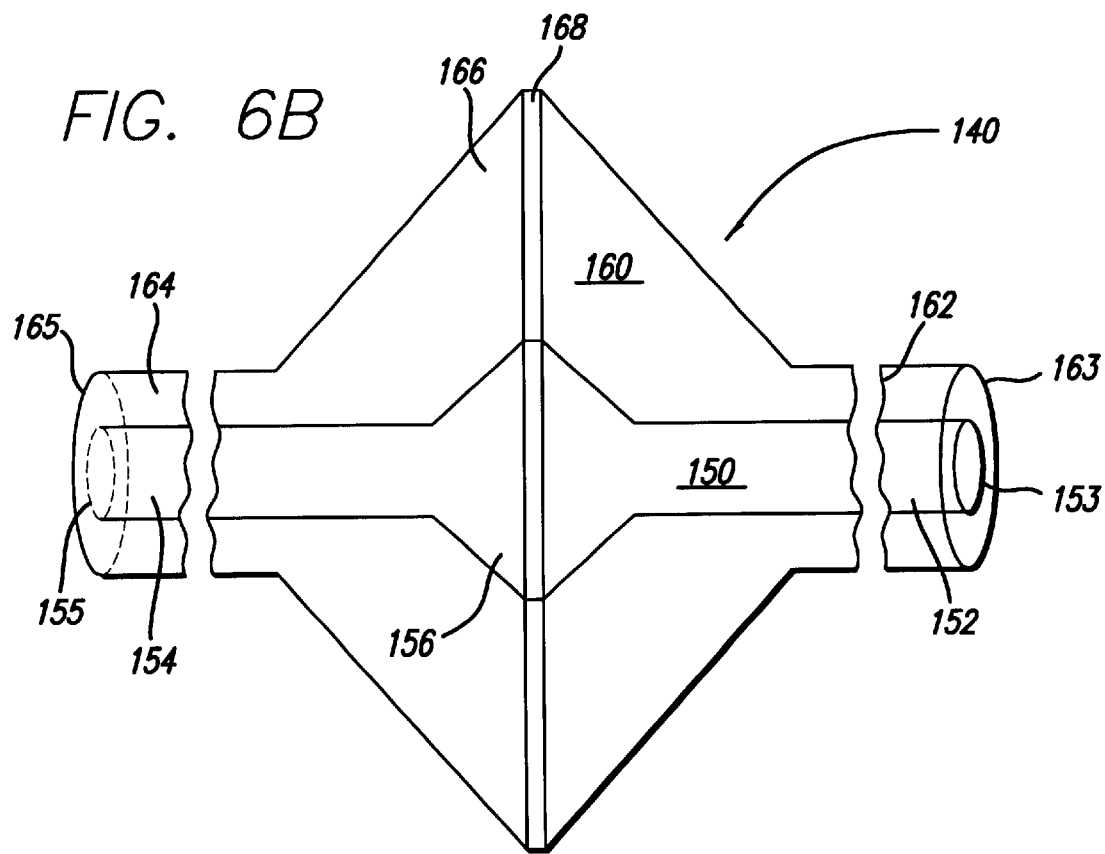
FIG. 6B is a perspective, partial cross-sectional view of an alternative embodiment of the coaxial filter device illustrated in FIG. 6A.

In an alternative embodiment shown in FIG. 6B, filters 158 and 168 can be coplanar, and may even be formed of a single filter disc passing from the inner wall of the outer filter chamber through the wall of the inner filter chamber. In yet another embodiment, inner tubular conduit 152 may axially extend from the end 163 of tubular conduit 162; the extension of tubular conduit 152 is sufficiently long to reach and sealably connect to the inspiratory port of a prior art proximal terminal, which lacks the inner conduit of the new proximal terminal of the present invention. An advantage of the coaxial filter is that one filter device may be used rather than two, using less space in shipping, use, and disposal.

With reference to FIG. 5B, an optional tubular extension 135 is illustrated which may be connected to end 137 of the inner pipe 134. Extension 135, when connected to end 137 is sufficiently long to reach and sealably connect to the inspiratory port of a prior art proximal terminal, which lacks the inner conduit of the new proximal terminal of the present invention.

In a preferred embodiment, the patient, or respiratory, conduit comprises a flexible tube with a diameter between 22 mm and 28 mm, and a length between 100 cm and 1.5 meters. If an inner tube is used with the aforementioned tube, the diameter (or D) is preferably between 11 mm and 15 mm. When using a single tube respiratory conduit, a 22 mm diameter is desirable for adult use, and a 15 mm diameter is desirable for pediatric use. When a coaxial conduit is used, a 28 mm diameter outer tube and 15 mm diameter inner tube are preferred. Single tube and coaxial respiratory conduit conventionally have standard slip fittings at at least one end for connection to other components to be used in an assisted ventilation system.

Dead space volume, $V_D$, in a tube is determined by the relationship:

$$V_D = \Pi(D/2)^2 \times L,$$

where L is the length of the dead space, and D is the outer conduit tube diameter. In a preferred embodiment, the first (outer) and second (inner) respiratory ports of the proximal terminal have inner diameters which are approximately equal to that of the outer tube and inner tube, respectively.

Likewise, the outer and inner conduits at the opposed ends of the coaxial filter have inner diameters which are preferably approximately equal to that of the outer tube and inner tube, respectively; and the outer and inner annuli (i.e., ends of pipes) of the proximal fitting have inner diameters which are preferably approximately equal to that of the outer tube and inner tube, respectively.

Thus, the present inventor has described a new unilimb artificial ventilation system, which includes a new patient conduit, a new coaxial filter, and a new proximal terminal, the latter of which may be incorporated into a new multifunctional interface. Various advantages and features of these inventions will be readily apparent to one of skill in the art; by way of non-limiting examples, these new devices are less expensive to manufacture; are easier to use, and have a wider range of uses and configurations than prior art systems; these new devices reduce medical wastes, since more components can be reused; yet, these devices are safer to use, due to the reduction of equipment required at the patient terminal, and provide for greater monitoring and control.

Artificial Ventilation Which Avoids Hypoxia and Hypocapnia

The unilimb artificial ventilation device of the present invention is ideal for providing artificial ventilation to a patient in which hypoxia is avoided while safely avoiding hypocapnia or even providing moderate hypercapnia. It was surprisingly discovered that normal carbon dioxide levels (normocapnia), or even moderate hypercapnia could be safely induced and/or maintained in a patient without causing hypoxia, as demonstrated by extensive data from human subjects, which dramatically illustrates this surprising discovery, and how the unilimb dead space volume can be adjusted to achieve normocapnia or moderate hypercapnia without causing hypoxia.

EXPERIMENTAL

Traditional methods of artificial hyperventilation using large tidal volume ($V_T$>10 ml/kg) and ventilatory frequency (f>10–12 breaths/min) inevitably result in a marked decrease in arterial blood carbon dioxide tension ($PaCO_2$), hypocapnia, and is often associated with serious adverse side effects.

Adverse effects of hypocapnia include: a) Vital organ tissue ischemia/hypoxia, since hypocapnia decreases cerebral, myocardial and splanchnic blood flow, and shifts the oxygen dissociation curve to the left, making the release of oxygen to the tissues difficult; b) Hypocapnia causes reduction of cardiac output and thus decreases the oxygen delivery (i.e. oxygen supply and availability to the tissues); c) Hypocapnia causes severe vasoconstriction of some tissues such as the skin; d) Hypocapnia causes blood and tissue biochemical disturbances: Anaerobic metabolism increases blood lactic acid concentration; and changes in plasma electrolytes (sodium, potassium, calcium, etc.) cause cardiac arrhythmias, metabolic acidosis, tetany, etc.

Therefore, studies were conducted to investigate the effects of ventilation apparatus dead space ($V_D$) on the arterial blood carbon dioxide tension ($PaCO_2$, "Pa" may be used interchangeably with "$P_a$"), and oxygen tension ($PaO_2$) during anesthesia. After institutional approval and patient consent, a total of 301 healthy (ASA class I) adult patients undergoing elective surgery were studied (divided into Study I of 241 patients, and Study II of 60 patients). Anesthesia was induced with a sleeping dose of thiopental; endotracheal (ET) intubation was facilitated with 1 mg/kg succinylcholine. Anesthesia was maintained with 60–70% nitrous oxide in oxygen and 0.5–1.0% halothane, or 0.8–1.5% enflurane, using a conventional anesthesia circle breathing system with $CO_2$ absorption. Intraoperative muscle relaxation was achieved with intermittent pancuronium bromide as required. The patients' lungs were mechanically ventilated using the traditional mode of intermittent positive pressure ventilation (IPPV) with the following ventilatory settings. Tidal volume ($V_T$=10 ml/kg), ventilatory frequency (f=10–12 breath/min), and inspiratory/expiratory ratio (I:E ratio=1:2) were kept constant throughout the study. $V_T$ was determined with a Wright respirometer placed at the ET tube. Fraction of inspired oxygen concentration ($F_iO_2$=0.3–0.4) was monitored using a galvanic oxygen analyzer (Riken OX-160, Japan). End-tidal $CO_2$ concentration was monitored using an infra-red $CO_2$ analyzer (AIKA, RAS-41, Japan).

After cardiopulmonary stabilization with the traditional mode of ventilation (i.e. no dead space; i.e., dead space external of the patient of less than 10 ml) was achieved, an arterial blood sample from a radial artery was obtained and immediate analysis of the blood sample was performed using an ABL2 blood gas analyzer (Radiometer, Copenhagen) for control measurement. After control values were taken, one or two of the predetermined dead space volumes, $V_D$, selected from 160, 200, 350, 510 and 550 (ml) was (or were) chosen randomly, and incorporated in the breathing circuit while the same artificial ventilation setting was maintained for 30 min. Thereafter, blood gas measurements were repeated for comparison and statistical analysis was performed. The results of Study I of 241 patients are summarized in Table I (divided into Group A, 60 kg±17; Group B, 65 kg±9; and Group C, 90 kg±8), and results of Study II of 60 patients in FIGS. 7–10.

Table 1 shows that the traditional mode of artificial ventilation using IPPV with no apparatus dead space inevitably resulted in a marked decrease in arterial carbon dioxide tension ($PaCO_2$) i.e., hypocapnia. Addition of dead space, $V_D$=160–200 ml, $V_D$=350 ml, and $V_D$=550 ml, significantly increased the $PaCO_2$ to normocapnic and moderate hypercapnic levels respectively, without evidence of substantial $PaO_2$ decreases, i.e. hypoxia, in any of the patients of Groups A, B and C. Study II shows a mathematical regression analysis of the blood gas data obtained from 60 patients (120 samples) during artificial ventilation with varied dead space volumes. Thus, it is demonstrated that a predetermined volume of dead space in the breathing

TABLE 1

Arterial Blood Gas Data Obtained From 241 Anesthetized Patients (318 samples) During Artificial Ventilation With or Without Apparatus Dead Space (Study I)

| Group | Number of Patients | Body Weight (Kg) | Dead Space Volume ($V_D$ in ml) | | | |
|---|---|---|---|---|---|---|
| | | | 0 | 160–200 | 350 | 550 |
| A | 172 | 60 ± 17 | Hypocapnia | Normocapnia | Moderate Hypercapnia | Moderate Hypercapnia |
| B | 61 | 65 ± 9 | | | | |

TABLE 1-continued

Arterial Blood Gas Data Obtained From 241 Anesthetized Patients (318 samples)
During Artificial Ventilation With or Without Apparatus Dead Space (Study I)

| | C | 8 Group | 90 ± 13 FiO$_2$ | Control | | | |
|---|---|---|---|---|---|---|---|
| PaCO$_2$ | A | | (0.3) | 32 ± 6 | | | |
| (mmHg) | B | | (0.3) | 33 ± 4 | 42 ± 9* | | |
| | C | | (0.3) | 34 ± 7 | | 46 ± 11* | 51 ± 8* |
| PaO$_2$ | A | | (0.3) | 169 ± 40 | | | |
| (mmHg) | B | | (0.3) | 163 ± 28 | 164 ± 22 | | |
| | C | | (0.3) | 178 ± 125 | | 212 ± 116* | 217 ± 137* |

Mean ± SD,
*p < 0.05 vs Control (V$_D$ = 0);
Ventilatory setting: V$_T$ = 10 ml/kg, f = 10–12 breath/min, I:E ratio = 1:2.

circuit can significantly control the PaCO$_2$ values without evidence of hypoxia during artificial ventilation, as illustrated in FIGS. 7–10 and Table 1. Maintenance of normocapnic levels may be highly desirable and beneficial to the patients during anesthesia and/or to patients undergoing artificial ventilation, for example in the ICU. As is clear from Table 1 and FIG. 10, the vast majority of patients will require an assisted ventilation system having a dead space of at least 100 cc, and in many instances of at least 160 cc, to obtain normocapnia while avoiding hypoxia, in accordance with the present invention.

FIG. 7 is a graphic illustration of the relationship between dead space volume, V$_D$, measured in milliliters per kilogram of patient body weight (ml/kg, or cubic centimeters per kg of body weight, cc$^3$/kg), and the resulting change in patient arterial carbon dioxide tension, P$_a$CO$_2$, (measured in mmHg), including a linear regression analysis curve, yielding a correlation coefficient, r, of 0.671, and a predicted value for the change in P$_a$CO$_2$ equal to the product of 2.621 times the V$_D$, plus 1.766, or in equation form:

$$\Delta P_aCO_2(mmHg) = (2.621 \times V_D(ml/kg)) + 1.766.$$

This illustrates that the change (Δ) in P$_a$CO$_2$ can be reliably predicted as a function of V$_D$ (when V$_D$ is between 0 and 8 ml per kg of patient weight, or cc$^3$/kg).

FIG. 8 is a graphic illustration of the independence of P$_a$CO$_2$ as V$_D$ is varied between about 0 and 8 ml/kg, including a linear regression analysis curve which shows no significant correlation (Ⓡ is only 0.074) between the two variables in the range tested. Thus, even when dead space volume is large enough to increase P$_a$CO$_2$ by 15 mmHg (see FIG. 7), there is no significant reduction in P$_a$CO$_2$.

Figures 9, 11:
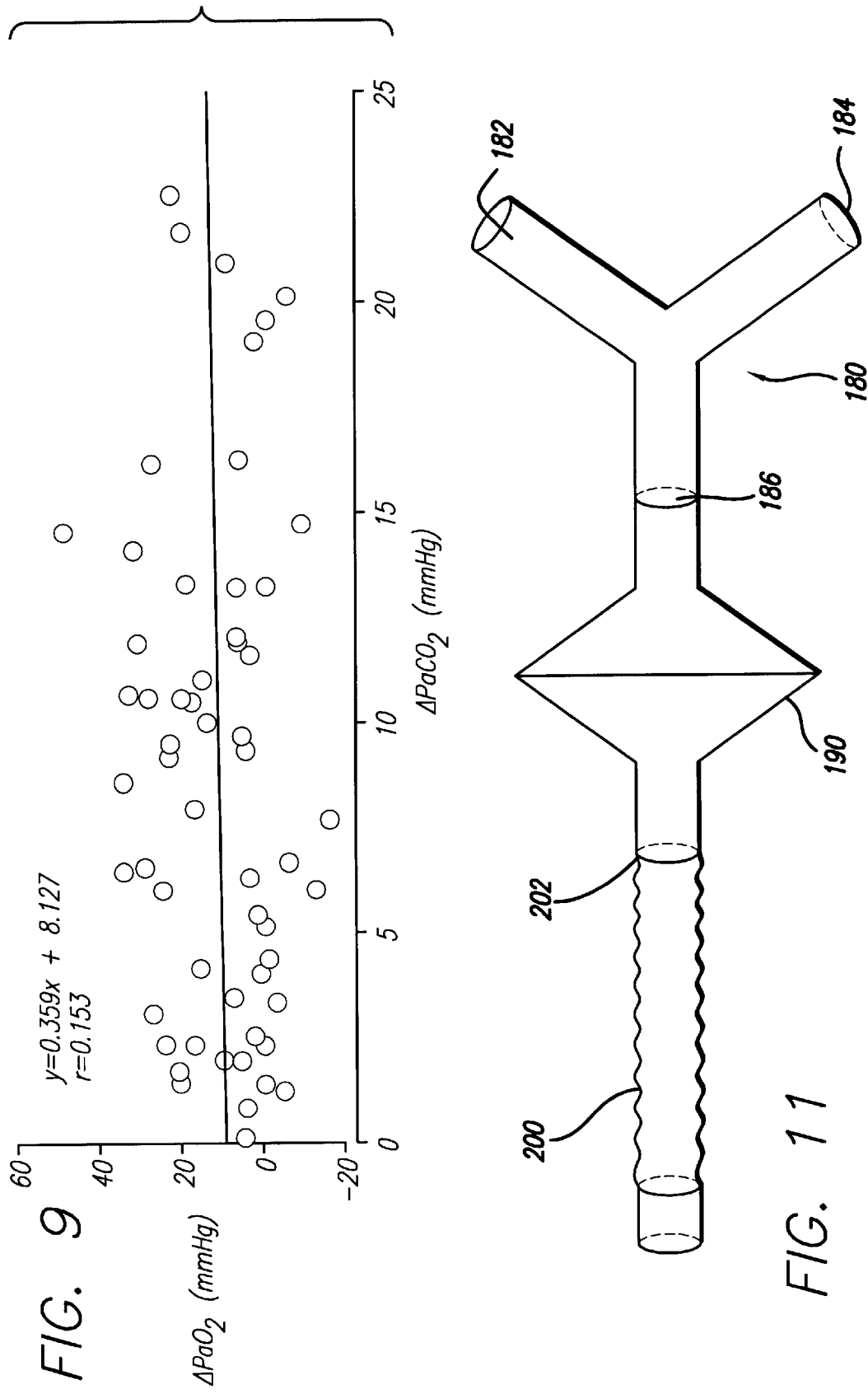
FIG. 9 is a graphic illustration of the independence of changes in $P_aCO_2$ and $P_aCO_2$ as $P_aCO_2$ was varied between 0 and 25 mmHg, including a linear regression analysis curve having a correlation coefficient, r, of 0.153, thus showing that increasing $P_aCO_2$ between 0 and 25 mmHg has no significant effect on $P_aCO_2$.
FIG. 11 is a plan view of an assisted ventilation system using a prior art dual hose fitting connected through a filter to a single patient conduit.

FIG. 9 is a graphic illustration of the independence of changes in P$_a$CO$_2$ and P$_a$CO$_2$ as P$_a$CO$_2$ was varied between 0 and 25 mmHg, including a linear regression analysis curve having a correlation coefficient, r, of 0.153, thus showing that increasing P$_a$CO$_2$ between 0 and 25 mmHg has no significant effect on P$_a$CO$_2$.

The table of FIG. 10 is generated by the results of data shown in the graph of FIG. 7 of Study II.

Thus, the artificial ventilation method of the present invention provides for increasing the dead space volume external to a patient to induce and/or maintain normocapnia or moderate hypercapnia while avoiding hypoxia. Without limiting the invention to any particular theory of operation, it is believed that the anatomical dead space present in a patient's respiratory system, including for example that formed by the upper airway (i.e., nose, mouth, laryngeal cavity), trachea and bronchial trees, is at least partially eliminated by endotracheal intubation devices. Thus, the amount of rebreathing from the anatomical dead space is reduced. Further, in order to avoid hypoxia and atelectasis in the prior art, inspiratory oxygen is provided at high pressure, large tidal volume and rapid respiratory rate; this results in hyperventilation and considerable reduction in concentration of arterial carbon dioxide.

In a preferred embodiment, the dead space volume in a unilimb patient respiratory conduit is adjusted to at least 10 ml (cc$^3$), or in an alternative embodiment to at least 30 ml, and may be adjusted to or in excess of 150 ml. The unilimb patient respiratory conduit used may be any of those described herein, or modifications thereto. Although use of the devices described herein is preferred for the foregoing artificial ventilation method, it is anticipated that the discovery that increased carbon dioxide does not necessarily cause hypoxia, so long as sufficient oxygen is provided, may lead to the use of other devices to provide artificial ventilation without hypocapnia or hypoxia. For example, carbon dioxide from an external source may be combined with the inspiratory gases, or a dual limb system may be used, in which additional carbon dioxide is supplied to the patient. For example, with reference to FIG. 11, a Y-shaped fitting 180 is illustrated, which has an input port 182, an exhaust port 184, and a respiratory port 186. Fitting 180 is connected at its distal end to a filter device 190. One way valves, not shown, are proximal of ports 182 and 184 to ensure intermittent positive pressure ventilation. A flexible tube 200 is attached at its proximal end 202 to the distal end of filter device 190. Thus, the entire internal volume of tube 200 serves as dead space. The length and diameter of tube 200 may be selected to achieve a predetenmined dead space.

Thus, the assisted ventilation method of the current invention, which avoids hypoxia and hypocapnia, can be provided in some instances with older assisted ventilation systems, while still having the advantages of a single tube for inspiratory and expiratory gases. Tube 200 and filter device 190 may be sealably bonded together, or separate easily attachable and detachable components. Tube 200 can be of varying predetermined lengths of uniform diameter for preselected dead space volume; tube 200 may have axial adjustable length, and have calibration markings at its opposed ends, the distance between the distal and proximal markings thereon precalculated to provide a predetermined dead space (in one embodiment, distal calibration markings can only be seen when the surrounding flexible pleated tubing is axially extended, and are not legible when the surrounding tube pleats are in their folded axially compressed state).

In a preferred embodiment, artificial ventilation is provided to a mammal (e.g., a human) sufficient to prevent hypoxia, while a sufficient portion of the mammal's expiratory gases are rebreathed to permit the arterial carbon dioxide tension of the mammal to be between about 35 mmHg and about 95 mmHg, and, in another preferred embodiment, the arterial carbon dioxide level of the mammal is kept between about 35 mmHg and about 45 mmHg (i.e., normocapnia).

Figure 12:
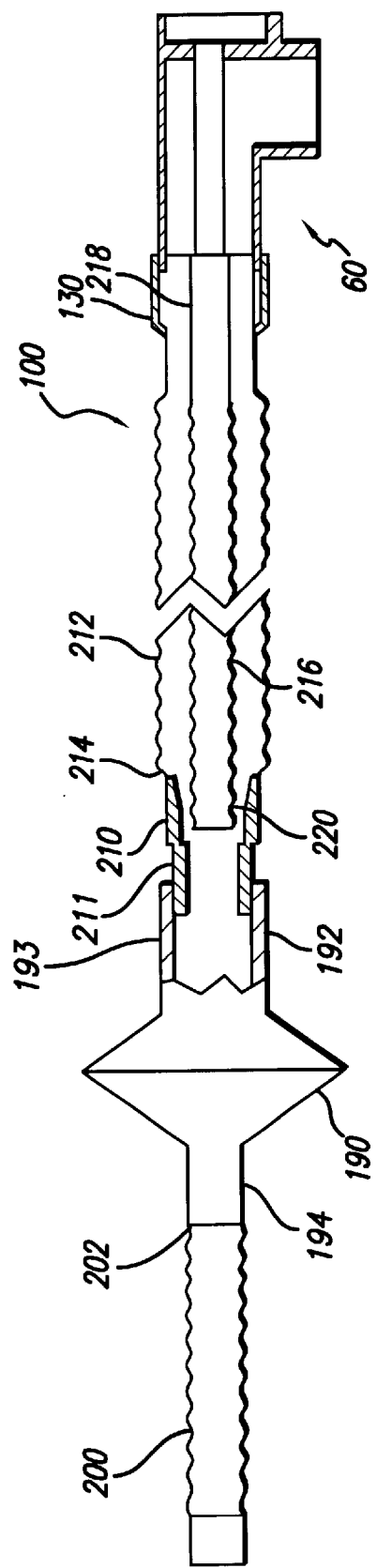
FIG. 12 is a partial cross-sectional view of the new proximal terminal illustrated in FIG. 3A connected to the detachable patient coaxial breathing conduit illustrated in FIG. 5A, which in turn is connected to a filter and a dead space tube.

With reference to FIG. 12, an alternative embodiment of the present invention is illustrated. Unilimb respiratory conduit 100 is connected at its proximal end to the distal end of proximal terminal 60 via proximal fitting 130. Unilimb respiratory conduit 100 has a distal terminal 210, to which is connected outer flexible tube 212 at its distal end 214. Inner flexible tube 216 is connected at its proximal end to inner pipe 218 of proximal fitting 130. The distal end 220 of inner flexible tube 216 may be free to move axially with respect to the distal end 214 of outer flexible tube 212, or the distal end 220 of inner flexible tube 216 may be connected to distal terminal 210, or the distal end 220 of inner flexible tube 216 may be prevented from extending beyond the distal end of outer flexible tube 212 (as possibly extended by distal terminal 210) by a stop (not shown) in distal terminal 210.

Figure 13:
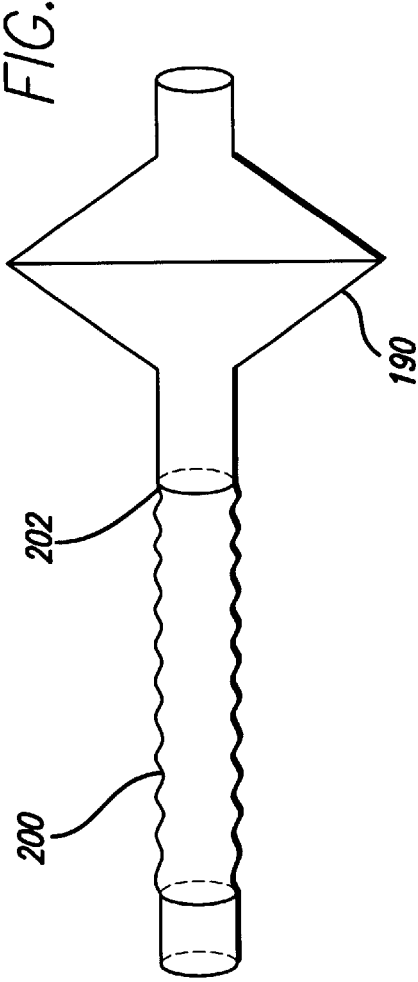
FIG. 13 is a plan view of a dead space tube connected to a filter.

Since the coaxial unilimb respiratory conduit 100 provides the advantages mentioned above, and may have substantial length so that it may reach from an assisted ventilation device located remote from the patient, it is desirable in some instances to reuse the coaxial unilimb respiratory conduit 100, or to add and/or adjust the dead space independent of coaxial unilimb respiratory conduit 100. Thus, filter 190 is detachably connected at its proximal end 192 to distal terminal 210. Filter 190 is detachably connected at its distal end 194 to proximal end 202 of flexible tube 200. Flexible tube 200 may have a predetermined dead space, or may have accordion-like folds therein to permit adjustment of the dead space volume. In one embodiment, filter 190 is permanently bonded to flexible tube 200, and the combination has a fixed dead space (i.e., the volume of the filter and tube combined). In another embodiment, calibration marks (such as 121 in FIG. 5A), can be placed on flexible tube 200, and these calibration marks may take into account the dead space volume of the filter (i.e., the filter volume is added to the volume of flexible tube 200). Thus, a user may dispose of filter 190 and tube 200 after a single use, and referring to FIG. 13, a combination filter 190 and tube 200 for single use is illustrated.

As is clear from the foregoing, in practice, a new assisted ventilation device is made by health care personnel for each patient from new disposable components in combination with reusable components. The disposable components and reusable components forming each assisted ventilation system are selected to match the unique needs of each patient. Thus, the present invention provides new components, new methods of providing components, and methods of making assisted ventilation systems.

The filter and dead space tube combination is a surprisingly valuable and useful device, as it was previously believed necessary to minimize dead space, yet the dead space in the filter and tube are intentionally made greater than what the inventors believe to have previously been provided. The surprising discovery that dead space can be used to achieve normocapnia or moderate hypercapnia without hypoxia creates substantial patient health and cost benefits. For example, by use of a filter and dead space tube in connection with an assisted ventilation device (e.g., ventilator), sufficient oxygenation can be provided to a patient while maintaining a substantially normocapnic state with a single tube. In certain instances, only the filter and the single tube (i.e., dead space tube) need be disposed of after use, thus creating substantial cost savings, and reducing medical wastes. In a preferred embodiment, the volume of the dead space in the dead space tube and/or filter when connected between a patient and an assisted ventilation device is sufficient to permit sufficient oxygenation to a patient while maintaining a normocapnic or moderate hypercapnic state. Preferably, the dead space volume in the dead space tube and/or the filter is between about 10 cubic centimeters and about 1000 cubic centimeters, and the flexible tubing forming the dead space tube has a diameter between about 11 millimeters and about 28 millimeters, and a length between about 5 centimeters and 1.5 meters. In an alternative embodiment, the dead space volume in the dead space tube and/or the filter is between about 50 cubic centimeters and about 1000 cubic centimeters, and the flexible tubing forming the dead space tube has a diameter between about 15 millimeters and about 28 millimeters, and a length between about 5 centimeters and 1.5 meters.

Thus, instead of requiring two tubes (one inspiratory and the other expiratory), a single tube serves as both an inspiratory and expiratory conduit. The present invention thereby creates a surprisingly beneficial and new method of providing unilimb respiratory conduits for use in providing assisted ventilation and making assisted ventilation systems, wherein the systems are constructed at the site of use by the user, users, and/or assistants thereto, by use of tubing having a predetermined dead space volume in the assisted ventilation system made for the patient. In one embodiment, tubing of predetermined fixed volume, or a range of volumes in the case of adjustable volume tubing (e.g., FLEXITUBE®) is provided to the user. The user merely needs to select a tube with the desired volume. In another embodiment, tubing may be sold in coils of great length, and cut to the desired size. Calibration marks may be made on the tubing to permit easier determination of the volume in a length thereof. The latter method is of course slower, and there is more room for human error. Thus, it is believed that health care personnel will prefer to use sections of tubing available at the site of use having premeasured standard volumes, or volume ranges, and the sections of tubing will preferably have either integral or attached fittings thereon to facilitate fabrication of the assisted ventilation system and operable connection to a patient.

In addition to providing new methods of making assisted ventilation systems, the present invention includes tubing for use in making assisted ventilation systems, of the new type described herein having a dead space therein sufficient that when used to provide assisted ventilation to a mammal maintains normocapnia or moderate hypercapnia without hypoxia, wherein the tubing has the length and diameter parameters needed to create the desired dead space volume and/or range of volumes. Thus, also included in the present invention are methods of providing tubing to users at the site of use for use in making such assisted ventilation systems.

COMPONENTS AND METHODS TO ENHANCE PATIENT SAFETY

One of the objects of the present invention, and modern medicine in general, is reducing biological and other types of contamination. as frequently there are greater health effects to patients from infection than from their underlying injuries. Filters create a barrier to contamination from a patient and the surroundings entering assisted ventilation devices, and likewise create a barrier to any contamination in assisted ventilation devices from being breathed in by patients. Nevertheless, it is possible that in the rush and pressure of assisting patients, a fresh filter will not be attached for each patient, or, in some cases, filters not meeting minimum filtration standards will be used. Further, while it may be desirable in some instances to reuse the coaxial patient respiratory conduit by using the disposable filter and dead space tube embodiment shown in FIGS. 12 and 13, after a period of time, moisture, nebulized pharmaceutical agents, and other chemicals may precipitate in the coaxial conduit, and/or contaminants may build up therein. Thus, referring to FIG. 12, it is desirable in some instances to ensure that coaxial unilimb respiratory conduit 100 is disposed of after a single use along with filter 190 and tube 200. In an alternative embodiment, a coaxial filter, such as that illustrated in FIGS. 6A or 6B may be inserted in the device of FIG. 12, wherein the proximal terminal 60 is separated from and operably connected to the coaxial unilimb respiratory conduit 100 by the coaxial filter of FIG. 6A or 6B.

Thus, with reference to FIGS. 12, 14, 15, 16, and 19, non-limiting examples of unique fittings are illustrated, which can be utilized to ensure that proper connections are made to proper devices, all with the design of maximizing patient well being, while also minimizing costs. Referring back to FIG. 12, filter 190 is detachably connected at its proximal end 192 to distal terminal 210. The cylindrical proximal terminating portion or proximal sleeve 193 of proximal end 192 has an inner diameter sized to friction fit over the outer diameter of the distal terminating portion or male fitting 211 of distal terminal 210. Either or both of proximal sleeve 193 and male fitting 211 may be tapered to facilitate connection therebetween; in another embodiment, the proximal sleeve 193 (or female fitting) and male fitting 211 have mating frustoconical shapes. By adjusting the size of proximal sleeve 193 and male fitting 21 , only components, such as dead space tubes with predetermined specifications (or patient airway devices, e.g., endotracheal tubes, laryngeal and other masks) having the proper sized proximal sleeves may be connected to a coaxial unilimb respiratory conduit such as that illustrated in FIG. 12.

Figure 14:
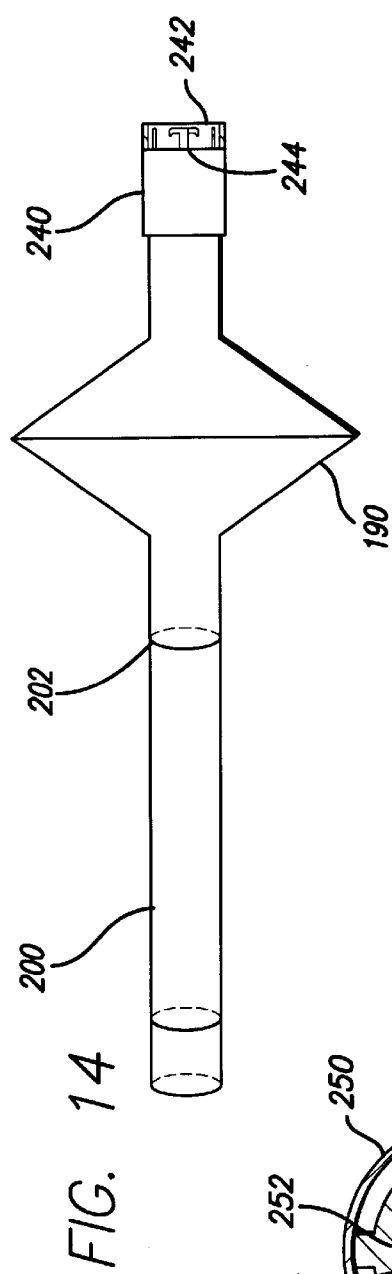
FIG. 14 is a plan view of an alternative embodiment of the device of FIG. 13 which includes a connector fitting at its proximal end.
Figure 15:
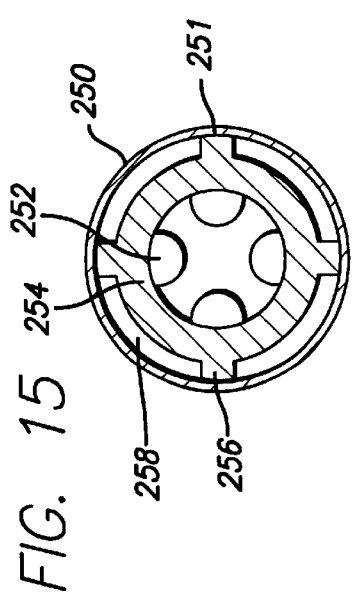
FIG. 15 is an end elevation view of a distal connector fitting for use in alternative embodiments of the present invention.

With reference to FIG. 14, an alternative embodiment of the present invention is illustrated, in which filter 190 is integrally connected to a proximal connector fitting 240. Filter 190 may also be a combination filter and HME device (heat and humidity exchanger). A partial cross section of cylindrical sleeve 242 is shown to permit a side view of hooks 244 (all connector fitting sleeves may be tapered or frustoconically shaped to facilitate connection). Referring to FIG. 15, an end elevation view of a distal connector fitting 250 for use in alternative embodiments of the present invention is illustrated. It is envisioned that all distal connectors may be used as proximal connectors and vice versa, and thus, the distinction between distal and proximal connector fittings is merely to facilitate description thereof. The fitting 250 may be, by way of non-limiting examples, integrally connected at the distal end of distal terminal 124 in FIG. 5A and 5B or distal terminal 210 in FIG. 12, or integrally connected at the distal end of proximal terminal 60, for example in place of flanges 76 on the distal end of the inner conduit 70, or may be integrally connected to the distal end of the outer conduit in FIG. 3A.

A plurality of inwardly facing flanges 252 are provided to block attempts to insert the ends of tubes or other devices, such as inappropriate dead space tubes and/or filters, into distal connector fitting 250. Thus, only devices which have a mating fitting, such as for example proximal connector fitting 240, can be connected to distal connector fitting 250.

Figure 16:
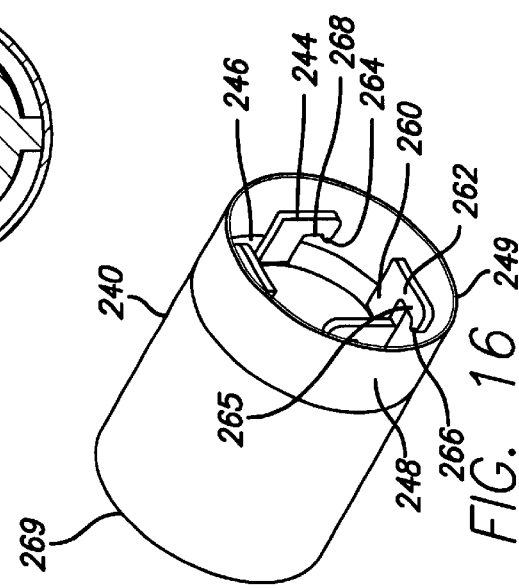
FIG. 16 is a perspective end elevation view of an adapter for use with the distal connector fitting of FIG. 15.

With reference to FIG. 16, an adapter comprising proximal connector fitting 240 is illustrated. Hooks 244 are annularly arranged about and connected to inward facing annular flange 246. A cylindrical sleeve 248 projects proximally from fitting 240, and has an inner diameter which approximately matches the outer diameter of distal connector fitting 250 (i.e., sleeve 248 and connector fitting 250 are shaped and sized to permit sleeve 248 to slidingly and sealably engage connector fitting 250). For example, the proximal edge 249 of cylindrical sleeve 248 may be tapered out to a larger diameter, and/or the distal edge 251 of distal connector fitting 250 may be tapered inward to a smaller diameter to facilitate a sealing slip connection of sleeve 248 over the distal edge 251. An annular flange 254 is connected near or at distal edge 251 in distal connector fitting 250 by tabs 256, thus creating an annular pattern of openings 258 about the periphery of annular flange 254.

Hooks 244 are formed of fingers 260 which project axially and proximally from annular flange 246, and terminate in retaining flanges 262. By axially aligning the proximal end of proximal connector fitting 240 with the distal end of distal connector fitting 250, hooks 244 may be aligned and inserted into openings 258. Counterclockwise rotation of fitting 240 with respect to fitting 250 causes one or more retaining flanges 262 to be latched behind one or more tabs 256, thus creating a more secure seal and grip between the fittings. Optional barbs or teeth 264 are shown in FIG. 16. In a preferred embodiment, when teeth 264 are used, the length of fingers 260 is just sufficient to axially project the retaining surface 265 of retaining flanges 262 so they may engage the proximal surface of tabs 256 when fitting 250 is fully axially inserted into fitting 240 and rotated. The teeth 264 have a tapered surface 266 to create a ramp, and hooks 244 and annular flanges 246 and 254 are sufficiently resilient to permit the teeth to slide over the proximal surface of tabs 256 upon relative counterclockwise rotation of fittings 240 and 250 and to thereby latch thereon. Each tooth has a locking surface 268, which permits the tooth to snap into the opening immediately counterclockwise of the opening in which its corresponding hook was inserted, which may provide a tactile and/or audible indication that the two fittings are fully engaged. Although hooks 244 are illustrated herein to permit the engagement of teeth 264 with tabs 256 upon relative counterclockwise rotation of fittings 240 and 250, the opposite arrangement is also contemplated. The ability to releasably lock fittings 240 and 250 together is dependent on the resilience of hooks 244 and annular flanges 246 and 254, the length of teeth 264, and the interaction of each locking surface 268 with the corresponding surface on the tab to which it is engaged. Thus, in one embodiment, teeth 264 serve to indicate that the fittings are fully engaged, while in another embodiment, the teeth 264 prevent the fittings 240 and 250 from being readily disconnected after the teeth are locked in place.

Figure 19:
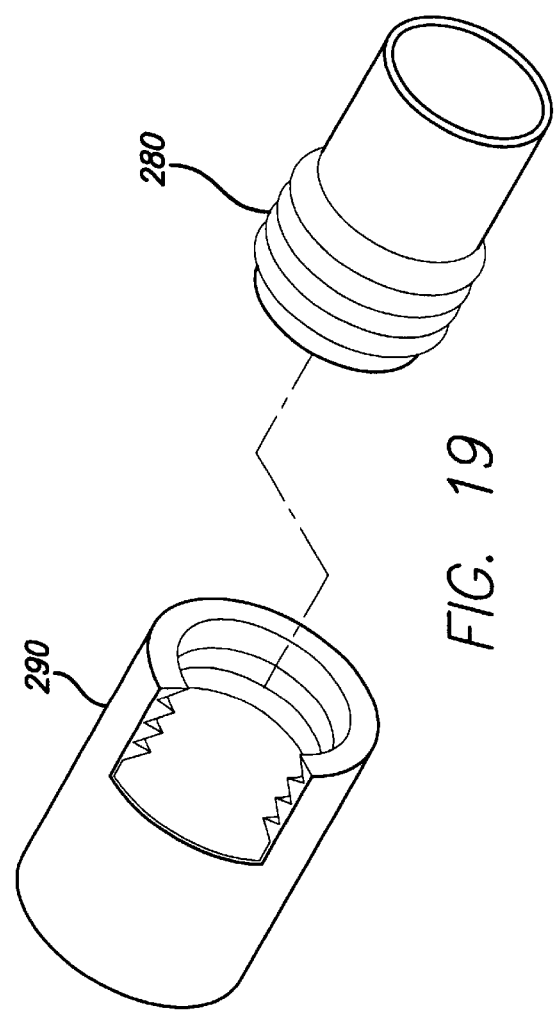
FIG. 19 is an exploded partial cross sectional partial plan view of a threaded adapter and the distal end of conduit including a mating threaded connector fitting.

With regard to FIG. 19, a male threaded fitting 280 and female threaded fitting 290 are illustrated. In this alternative embodiment, corresponding threaded fittings permit only matching components to be attached. For example, threaded fitting 280 may be integrally attached or bonded to the distal end of the inner conduit 70 of proximal terminal 60. Only filters, tubing and/or other devices have a mating threaded fitting 290 at the proximal end thereof may be connected to threaded fitting 280.

As is apparent from the foregoing, manufacturers of filters, patient airway devices (e.g., masks, endotracheal tubes, etc.), HMEs, water traps. nebulizers, etc., provided they meet minimum standards, may produce such devices with the appropriate fitting 240 or 250 integrally connected thereto, depending respectively if it is to be connected to fitting 250 or 240, or analogously fittings 280 and 290 or other appropriate matching fittings may be used. In order to retrofit devices meeting minimum standards, adaptors, such as that shown in FIG. 16, may be provided, which have a mating connector at one end for the patient respiratory conduit or other device to which they are to be connected, and having a standard slip connector on the other end to attach to the device to be retrofitted. In a preferred example, adapters, such as shown in FIG. 16, have a first end 269 meeting international standards and a second end meeting the particular fitting requirements.

Figure 17:
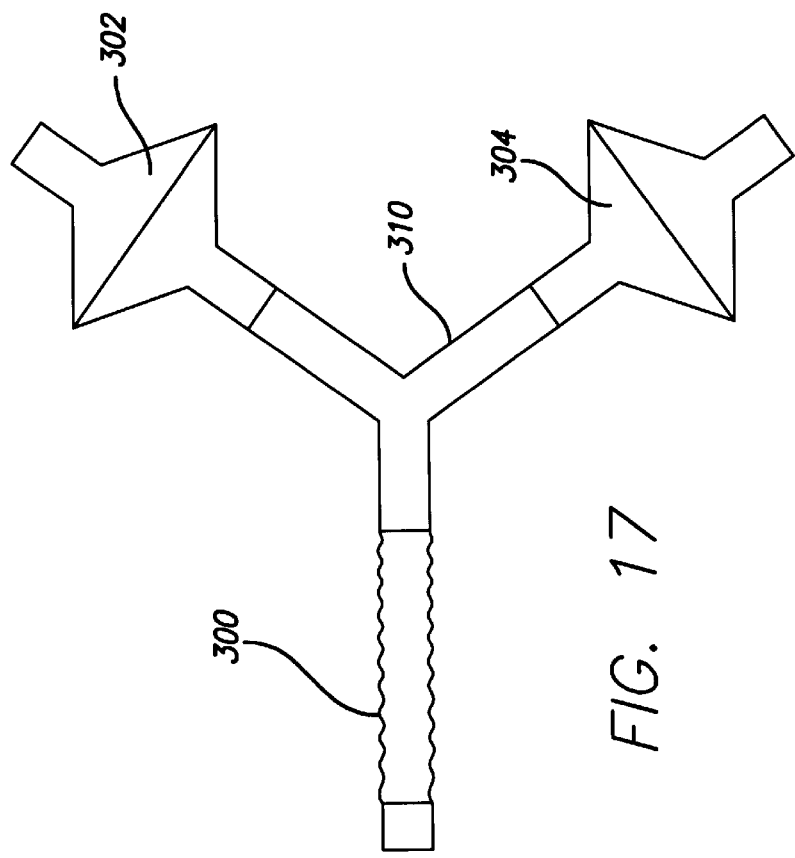
FIG. 17 is a plan view of an assisted ventilation system using a prior art dual hose fitting connected at its proximal ends to two filters and at its distal end to a single patient conduit.

As is implicit and/or explicit from the foregoing, numerous configurations of assisted ventilation systems are embodied in the present invention. For example, with reference to FIG. 17, an alternative embodiment of the present invention is illustrated which uses a prior art dual hose fitting 310 connected at its proximal ends to two filters 302 and 304 and at its distal end to a single tube patient conduit 300. In view of the surprising discovery that dead space contained within the single tube patient conduit (along with whatever dead space exists in the dual hose fitting and the other devices in the assisted ventilation system) can be utilized to simultaneously prevent hypocarbia while providing sufficient oxygenation, it is envisioned that single tube patient conduits (also referred to herein as dead space tubes), each having a predetermined dead space volume, or each having a range of dead space volumes, will be provided as a separate components. Note that due to the proximal placement of filters 302 and 304, both filters and all components distal thereof will be contaminated by contact with a patient, and thus may require disposal and/or sterilization after each use.

In accordance with the present invention, a method is provided in one embodiment to cut tubing from a much longer length, perhaps a roll or coil, to the desired length at the site of use to achieve a desired dead space volume, or range of safe volumes in the cases of pleated tubing (e.g., FLEXITUBE®). By having tubes of predetermined volumes ready, there is less likelihood of a mistake being made in cutting tubing to a desired length, and also increases the safety and rate of making an assisted ventilation device in accordance with the present invention.

Figure 18:
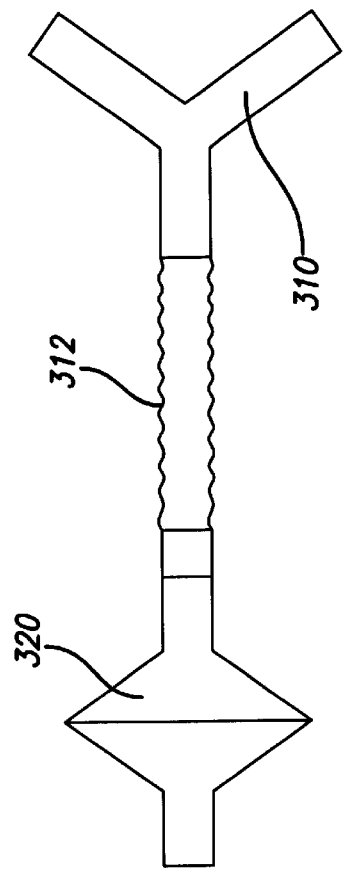
FIG. 18 is a plan view of an assisted ventilation system using a prior art dual hose fitting connected to a single patient conduit at its distal end, and having a filter connected at the distal end of the single patient conduit.

FIG. 18 is a plan view of an assisted ventilation system using a prior art dual hose fitting 310 connected to a single patient conduit 312 at its distal end (dead space tube), and having a filter 320 connected at the distal end of conduit 312. In this embodiment, only one filter 320 is used, which may provide for less waste, as it is possible, in certain instances, to only dispose of filter 320 after use, without disposing of tube 312 and fitting 310. Dead space tube may also be referred to as a normocapnic (or moderate hypercapnic) breathing tube, with it being understood that such tubes in accordance with the present invention have a predetermined volume, or range of volumes, sufficient to prevent hypoxia when utilized to provide assisted ventilation while also maintaining normocapnia or a desired level of carbon dioxide rebreathing.

With reference to FIG. 20, proximal terminal 60, as described in more detail above with reference to FIG. 3A is connected to a single patient conduit 340. Thus, the entire volume of conduit 340 is dead space. In this embodiment, proximal terminal 60 and conduit 340 are not protected by a filter. Thus, it is anticipated that the embodiment of FIG. 20 would be used with a filter 360, and/or with two separate filters attached to the inspiratory gas inlet and expiratory gas outlet. FIG. 21 shows a proximal terminal 60 connected to the proximal end of a patient conduit 340 with a filter 360 connected to the distal end of conduit 340. In the case shown in FIG. 20, it may be possible to reuse proximal terminal 60 and conduit 340 by only attaching a fresh filter 360. FIG. 22 shows a proximal terminal 60 connected to the proximal end of a filter 360 with a patient conduit 340 connected to the distal end of filter 360. In the case shown in FIG. 21, it may be possible to reuse proximal terminal 60 by attaching a fresh filter 360.

Because of the features of proximal terminal 60, in one embodiment, proximal terminal 60 forms part of, and is integral with, the reusable components of an anesthesia machine and/or assisted ventilation device. When proximal terminal 60 forms part of, and is integral with, the reusable components of an anesthesia machine and/or assisted ventilation device, it is preferably provided with means for preventing connection thereto without proper filtration means. Thus, unique connector fittings, such as those illustrated in FIGS. 15, 16 and 19 may be utilized. In a preferred embodiment, all components, including at least one filter, operably attached to proximal terminal 60 are disposable and lockingly engaged together, thus ensuring that patient safety is maximized by requiring disposal of all of the disposable components together after a single use. For example, by providing proximal terminal 60 with a unique distal connector, only a proper filter, having a mating proximal connector, can be attached thereto. Likewise, the filter is provided with a unique distal connector, which permits only permanent locking engagement with single use tubing and/or devices leading to the patient. After use, the filter and components connected thereto are disposed of, since the permanent locking engagement of the components prevents disengagement thereof without damage thereto. Proximal terminal 60 can have other shapes than that illustrated herein. For example, additional ports and conduits can be added thereto, the shape of the housing altered, and the location of ports and conduits connected thereto altered.

While preferred embodiments of the invention have been illustrated and described in detail in the figures and foregoing description, the same is to be considered as illustrative and not restrictive in character. For example, while tubes of circular cross-section are used herein, it is anticipated that tubular conduits of varying cross-sectional shape may be used, and that the inner tube of a coaxial tube may or may not be axially centered within the outer tube, or only portions of the inner tube may be axially centered in the outer tube while other portions may be off center. It is also envisioned that the proximal terminal may have more than two conduits passing therethrough, which may connect to a flexible respiratory conduit having more than two lumens. In place of the push, twist and lock fittings of the present invention, spring biased clips may be provided on the distal end of one component, which snap onto corresponding tabs on the proximal end of another component, or vice versa (the tabs and/or clips may have tapered surfaces so that, when pressed against each other, the clips will bend in order to receive the tabs). Thus, it is understood that only the preferred embodiments have been shown and described, and that all changes and modifications that come within the spirit of the invention are desired to be protected.

what is claimed is:

1. An assisted ventilation system for use in mammals to provide thereto and exhaust therefrom respiratory gases, comprising:
   a first breathing conduit for providing and exhausting respiratory gases from a mammal, said first breathing conduit having a proximal end and a distal end and being flexible and axially extendable and compressible to provide a variable deadspace, interface means for providing gases to be inspired and for receiving expired gases, said interface means comprising a proximal terminal operably connected to said proximal end of said first breathing conduit, means for preventing biological contamination from communication with said interface means, said means for preventing biological contamination being operably connected to said first breathing conduit, said proximal terminal comprising a rigid housing, said housing comprising an inspiratory gas input, an expiratory gas outlet, and a first respiratory port, said inspiratory gas input and said expiratory gas outlet being in fluid communication with said first breathing conduit via said first respiratory port when said breathing conduit is in operable connection with said interface means, wherein said first breathing conduit is operably detachable from said interface means for disposal or sterilization after use by a user at the site of use.

2. A unilimb respiratory conduit for use in an assisted ventilation system, comprising:

an outer flexible tube, an inner flexible tube, said outer flexible tube and inner flexible tube each having a proximal end and a distal end; the outer diameter of said inner flexible tube being smaller than the inner diameter of said outer flexible tube, said inner flexible tube being at least partially disposed within said outer flexible tube, said distal end of said inner flexible tube being disposed within and in direct fluid communication with said outer flexible tube, and a proximal fitting, said proximal fitting comprising an inner pipe and an outer pipe maintained in fixed coaxial spaced relationship by spacing means, said outer pipe and inner pipe each having a proximal end and a distal end, wherein said distal end of said inner pipe is operably connected to said proximal end of said inner flexible tube and said distal end of said outer pipe is operably connected to said proximal end of said outer flexible tube, said proximal end of one of said pipes capable of being operably connected to an inspiratory gas input while said proximal end of the other one of said conduits is operably connected to an exhaust outlet, and wherein said distal end of said outer flexible tube can be operably connected to an airway device connected to a mammal, and wherein a user may utilize said unilimb respiratory conduit in an assisted ventilation system via operative connection thereto via said proximal fitting in order to use said unilimb respiratory conduit to provide inspiratory gases and exhaust expiratory gases from a mammal, and may disconnect said unilimb respiratory conduit from the assisted ventilation system after use by detaching said proximal fitting, and further comprising:

filter means, and a dead space tube, said dead space tube having a distal end and a proximal end, wherein said proximal end of said dead space tube can be operably connected through said filter means to said distal end of said outer flexible tube, wherein, when said proximal end of said dead space tube and said filter means are operably connected to said distal end of said outer flexible tube, said distal end of said unilimb respiratory conduit is operably connected to a mammal, and said proximal end of said unilimb repiratory conduit is operably connected to a source of inspiratory gases, inspiratory and expiratory gases may pass through said filter means, and inspiratory and expiratory gases may mix in said dead space tube.

3. A respiratory conduit device for use in an assisted ventilation system, comprising:

a flexible tube and a filter, said tube having a proximal end and a distal end, wherein said proximal end may be placed in fluid communication with a source of inspiratory gas through said filter means and said distal end may be placed in fluid communication with a mammal to provide a conduit for inspiratory and expiratory patient gases, or said distal end may be placed in fluid communication with a mammal through said filter means and said proximal end may be placed in fluid communication with a source of inspiratory gas to provide a conduit for inspiratory and expiratory gases, wherein said respiratory conduit device can be operatively connected by a user at the site of use to an assisted ventilation system and detached by a user after use for independent sterilization or disposal, wherein, when said device is operably connected to a mammal, dead space contained within that portion of said respiratory conduit device external of the mammal is between about 40 cubic centimeters and about 1000 cubic centimeters.

4. The respiratory conduit device of claim 3, wherein said flexible tube has a diameter between about 15 millimeters and about 28 millimeters and a length between about 5 centimeters and about 1.5 meters, and is axially extendable and compressible to provide a variable deadspace.

5. The respiratory conduit device of claim 3, wherein said flexible tube has calibration markings that permit determination of the volume of the dead space within said device.

6. A method of providing unilimb respiratory conduits for use in assisted ventilation systems, comprising the step of:

providing at least one unilimb respiratory conduit to at least one user for use thereby in administering and exhausting gases from a mammal, wherein said unilimb respiratory conduit comprises a flexible tube that can be readily operably connected at a first end to a mammal and at a second end to a terminal housing forming part of an assisted ventilation system by the user for administering and exhausting respiratory gases from the mammal, said unilimb respiratory conduit being readily disconnected from the terminal housing after use, said unilimb respiratory conduit for use with a terminal housing having at least two independent flow paths therein which are capable of simultaneous operative connection to a respiratory conduit and which diverge to form an inlet port at a second location and an outlet port at a third location in the terminal housing, said second end of said unilimb respiratory conduit being operably connectable to the first location in the terminal housing, wherein said unilimb respiratory conduit can be provided with or separately from the terminal housing, said flexible tube being axially extendable and compressible to provide a variable deadspace therein, wherein, when said unilimb respiratory conduit is operably connected to a terminal housing and to a mammal so that inspiratory gases to and expiratory gases from the mammal pass therethrough, the dead space volume in said unilimb respiratory conduit is sufficient to maintain the mean arterial carbon dioxide tension of the mammal between about 35 mmHg and about 95 mmHg without causing hypoxia in the mammal.

7. The method of claim 6, wherein said unilimb respiratory conduit is provided for single use, and the terminal housing for which said conduit is provided for use therewith is reusable.

8. The method of claim 6, further comprising the step of providing a filter which may be readily operably connected to and disconnected from said respiratory conduit to create a barrier to biological contamination of the terminal housing from a mammal when a mammal is to be operably connected to said respiratory conduit and the terminal housing.

9. The method of claim 6, wherein said unilimb respiratory conduit comprises calibration means for determining the dead space therein.

10. The method of claim 6, wherein said at least one unilimb respiratory conduit is provided to one of the group consisting of a health care provider, an ICU, and a location where surgery can be performed.

11. A unilimb respiratory conduit for use in an assisted ventilation system, comprising:

a respiratory conduit which can be operatively connected by a user at the site of use to an assisted ventilation system and detached by a user after use for independent sterilization or disposal, said respiratory conduit comprising a flexible tube having a first end and a second end, wherein said first end can be operably connected to a mammal and said second end can be operably connected to an assisted ventilation system to carry inspiratory gases to the mammal and to receive expiratory gases from the mammal, wherein said tube has a variable length for permitting a user to vary the dead space volume of said respiratory conduit by axial extension or contraction thereof, wherein said flexible tube has a diameter between about 11 millimeters and about 28 millimeters, and a length between about 5 centimeters and about 1.5 meters wherein, when said respiratory conduit is operably connected into an assisted ventilation system and said system is operably connected to a mammal, said respiratory conduit has a dead space volume external of the mammal that can be adjusted to exceed about 40 cubic centimeters and to be less that about 1000 cubic centimeters.

12. The respiratory conduit of claim 11, wherein said unilimb respiratory conduit has calibration markings that permit determination of the volume of the dead space within said unilimb respiratory conduit.

13. The respiratory conduit of claim 11, wherein said tube contains at least one of the group consisting of an anesthetic gas, and oxygen provided via an assisted ventilation system.

14. The respiratory conduit of claim 13, wherein said tube is operatively connected to an assisted ventilation system.

15. The respiratory conduit of claim 11, wherein said tube is operatively connected to an assisted ventilation system.

16. The respiratory conduit of claims 11, wherein when said tube is operably connected into an assisted ventilation system and to a mammal so that inspiratory gases to and expiratory gases from the mammal pass therethrough, the dead space volume in said unilimb respiratory conduit is sufficient to maintain the mean arterial carbon dioxide tension of the mammal between about 35 mmHg and about 95 mmHg without causing hypoxia in the mammal.

17. The respiratory conduit of claim 11, wherein, when said tube is operably connected into an assisted ventilation system and to a mammal so that inspiratory gases to and expiratory gases from the mammal pass therethrough, the dead space volume in said unilimb respiratory conduit is greater than 100 cubic centimeters and less than a volume which will cause hypoxia in the mammal.

18. The respiratory conduit of claim 11, wherein, when said tube is operably connected into an assisted ventilation system and to a mammal so that inspiratory gases to and expiratory gases from the mammal pass therethrough, the dead space volume in said unilimb respiratory conduit is greater than 160 cubic centimeters and less than a volume which will cause hypoxia in the mammal.

19. An assisted ventilation system, comprising a respiratory conduit for carrying inspiratory gases to a mammal and for exhausting expiratory gases therefrom, wherein, when said system is operably connected to a mammal, said system has a dead space volume external of the mammal in excess of about 100 cubic centimeters, said dead space volume being less than a volume which will cause hypoxia in the mammal, wherein said respiratory conduit can be operatively connected by a user at the site of use into said assisted ventilation system and detached by a user after use for independent sterilization or disposal, said respiratory conduit comprising a flexible tube having a first end and a second end, wherein said first end can be operably connected to a mammal and said second end can be operably connected into said assisted ventilation system to carry inspiratory gases to the mammal and to receive expiratory gases from the mammal, wherein said tube has a variable length for permitting a user to vary the dead space volume of said respiratory conduit by axial extension or contraction thereof, wherein said flexible tube has a diameter between about 11 millimeters and about 28 millimeters, and a length between about 5 centimeters and about 1.5 meters.

20. An assembly for use in providing inspiratory gases to a patient and receiving expiratory gases therefrom, comprising a respiratory conduit and a proximal terminal, said respiratory conduit having a distal end and a proximal end and said proximal terminal having a distal end and a proximal end, wherein said distal end of said respiratory conduit is operatively connectable to and detachable from a patient by a user at a site of use, and said proximal end of said conduit is operatively connectable to and detachable from said proximal terminal by a user at a site of use, wherein said proximal terminal has first and second lumens defining respective first and second flow paths, said first and second lumens being independent of each other and each having a distal end and a proximal end, said distal ends of said lumens capable of simultaneous operative connection to said proximal end of said respiratory conduit and wherein said first and second flow paths in said proximal terminal diverge from each other proximally of said distal end of said proximal terminal so that said proximal end of said first lumen may be independently operatively connected to an inlet for a source of inspiratory gas while said proximal end of said second lumen may be independently operatively connected to an expiratory outlet, wherein said respiratory conduit may be operatively detached from said proximal terminal after use therewith for independent disposal or sterilization.

21. The assembly of claim 20, further comprising a common lumen, wherein said first flow path and said second flow path merge together at the distal ends of said lumens to form a common flow path, wherein said common lumen can be placed in operative fluid communication with said respiratory conduit.

22. The assembly of claim 20, wherein said first lumen and said second lumen are coaxial in said distal end of said proximal terminal and said third and fourth lumens are formed by coaxial tubes.

23. The assembly of claim 20, wherein said proximal terminal is permanently connected to an anesthesia machine or to a respirator type device, wherein a respiratory conduit may be operatively detached from said anesthesia machine or respirator type device after use therewith for disposal or sterilization.

24. A method for constructing a breathing circuit having a proximal terminal and a respiratory conduit, wherein the respiratory conduit has a distal end and a proximal end, the distal end of the conduit being operatively connectable to and detachable from a patient by a user at a site of use, and the proximal end of the conduit is operatively connectable to and detachable from a proximal terminal by a user at a site of use, and wherein the proximal terminal has first and second lumens defining first and second flow paths that are independent of each other and converge at a distal end of the proximal terminal so as to be capable of simultaneous operative connection to the proximal end of the respiratory conduit and wherein the first and second flow paths in the proximal terminal diverge from each other proximally of the distal end of the proximal terminal so that the first lumen of the proximal terminal may be independently operatively connected to an inlet for a source of inspiratory gas while the second lumen of the proximal terminal may be independently operatively connected to an expiratory outlet, and wherein the respiratory conduit has third and fourth lumens defining respectively a third flow path and a fourth flow path, the third flow path and the fourth lumen being independent of each other and each having a distal end and a proximal end, said method comprising operatively connecting the respiratory conduit to the proximal terminal so that the distal end of the third lumen is placed in fluid communication with the proximal end of the first lumen and the distal end of the fourth lumen is placed in fluid communication with the proximal end of the second lumen so that said third lumen may be operatively connected to an inlet for a source of inspiratory gas via the proximal terminal while said forth lumen may be operatively connected to an expiratory outlet via the proximal terminal, said operatively connecting of the respiratory conduit to the proximal terminal step permitting for the respiratory conduit to be detached from the proximal terminal at a site of use for disposal or sterilization of the respiratory conduit independent of the proximal terminal.

\* \* \* \* \*